US007118738B2

(12) United States Patent
Schlom et al.

(10) Patent No.: US 7,118,738 B2
(45) Date of Patent: Oct. 10, 2006

(54) RECOMBINANT POX VIRUS FOR IMMUNIZATION AGAINST MUC1 TUMOR-ASSOCIATED ANTIGEN

(75) Inventors: Jeffrey Schlom, Potomac, MD (US); Judith Kantor, Rockville, MD (US); Donald Kufe, Wellesley, MA (US); Dennis Panicali, Acton, MA (US); Linda Gritz, Somerville, MA (US)

(73) Assignees: Therion Biologics Corporation, Cambridge, MA (US); Dana-Farber Cancer Institute, Boston, MA (US); The United States of America as represented by the Department of Health and Human Services, Washington, DC (US)

( * ) Notice: Subject to any disclaimer, the term of this patent is extended or adjusted under 35 U.S.C. 154(b) by 21 days.

(21) Appl. No.: 10/057,136

(22) Filed: Jan. 25, 2002

(65) Prior Publication Data
US 2003/0021770 A1 Jan. 30, 2003

Related U.S. Application Data

(63) Continuation of application No. 09/366,670, filed on Aug. 3, 1999, now abandoned, which is a continuation of application No. PCT/US98/03693, filed on Feb. 24, 1998.

(60) Provisional application No. 60/038,253, filed on Feb. 24, 1997.

(51) Int. Cl.
*A01N 63/00* (2006.01)
*A61K 48/00* (2006.01)
*C12N 15/00* (2006.01)
*C12N 15/09* (2006.01)
*C12N 15/63* (2006.01)
*C12N 15/70* (2006.01)
*C12N 15/74* (2006.01)

(52) U.S. Cl. .................. 424/93.2; 435/320.1
(58) Field of Classification Search ............ 435/320.1, 435/456, 455; 424/93.1, 199.1, 93.2, 93.21
See application file for complete search history.

(56) References Cited

U.S. PATENT DOCUMENTS 5,942,235 A * 8/1999 Paoletti .................. 424/232.1

FOREIGN PATENT DOCUMENTS

| WO | WO 95 03825 | 2/1995 |
| WO | WO 96 10419 | 4/1996 |
| WO | WO 97 40182 | 10/1997 |

OTHER PUBLICATIONS

Scholl et al. Journal of Immunotherapy 23:570-580, 2000.*
Bronte et al. Journal of Immunology 154:5282-5292, 1995.*
Gunaburg et al. Molecular Medicine Today 1:410-417, 1995.*
Acres RB et al. Journal of Immunotherapy 14:136-143, 1993.*
Akagi, J. et al., J. Immunother. 20: 38-47 (1997).
Balloul, J.-M. et al., Cell. Mol. Biol. 40 (Sup.1): 49-59 (1994).
Bizouarne, N. et al., Breast Cancer Advances in Biology and Therapeutics; F. Calvo, M. Crepin, H. Magdelenat, eds.; John Liberty Eurotext, vol. 21: 308-8 (1996).
Graham, R.A. et al., Cancer Immunol. Immunther. 42: 71-80 (1996).
Taylor-Papadimitriou, J and Epenetos, A., Tibtech 12: 227-33 (1994).

* cited by examiner

*Primary Examiner*—Brian Whiteman
(74) *Attorney, Agent, or Firm*—Nixon Peabody LLP

(57) ABSTRACT

Recombinant pox viruses capable of expressing an immunogenic fragment of the MUC1 tumor-associated antigen are disclosed. The recombinant viruses can be used as vaccines to prevent the establishment of or treat tumors or pre-tumorous cells expressing the MUC1 tumor-associated antigen. The vaccines can be provided as an admixture comprising: (1) a recombinant pox virus encoding the immunogenic fragment of the MUC1 tumor-associated antigen, and (2) a recombinant pox virus encoding a T-cell co-stimulatory factor. The vaccine admixture can be used, e.g., to prevent establishment of tumors or pre-tumorous cells expressing the MUC1 tumor-associated antigen. The MUC1 specific cytotoxic T-cells can be isolated and expanded and used in a method for treating a host having a tumor expressing MCU1 positive tumor cells.

37 Claims, 5 Drawing Sheets

RECOMBINANT POX VIRUS FOR IMMUNIZATION AGAINST MUC1 TUMOR-ASSOCIATED ANTIGEN

The following application is a continuation of U.S. Ser. No. 09/366,670 filed on Aug. 3, 1999, now abandoned which is a continuation of PCT/US98/03693 filed on Feb. 24, 1998, now abandoned, which claimed benefit under 35 U.S.C. 119 of U.S. Provisional Application 60/038,253 filed on Feb. 24, 1997.

BACKGROUND OF THE INVENTION

The immunotherapeutic approach to the treatment of cancer is based on the observation that human tumor cells express a variety of tumor-associated antigens (TAAs) that are not typically expressed in normal tissues. These antigens, which include viral tumor antigens, cellular oncogene proteins, and tumor-associated differentiation antigens, can serve as targets for the host immune system and elicit responses which result in tumor destruction. This immune response is mediated primarily by lymphocytes; T cells in general and class I MHC-restricted cytotoxic T lymphocytes in particular play a central role in tumor rejection. Hellstrom, K. E., et al., (1969) Adv. Cancer Res. 12:167–223; Greenberg, P. D. (1991) in Advances in Immunology, vol. 49 (Dixon, D. J., ed.), pp. 281–355, Academic Press, Inc., Orlando, Fla. Unfortunately, as evidenced by the high incidence of cancer in the population, the immune response to neoplastic cells often fails to eliminate tumors. The goal of active cancer immunotherapy is the augmentation of anti-tumor responses, particularly T cell responses, in order to effect complete tumor destruction.

Most attempts at active immunization against cancer antigens have involved whole tumor cells or tumor fragments. However, the cloning of TAAs recognized by CD8+ T cells has opened new possibilities for the immunotherapy of cancer based on the use of recombinant or synthetic anti-cancer vaccines. Boon, T., et al., (1994) Annu. Rev. Immunol. 12:337–365; Brithcard, V., et al., (1993) J. Exp. Med. 178:489–495; Cox, A. L., et al., (1994) Science 264: 716–719; Houghton, A. N. (1994) J. Exp. Med. 180:1–4; Pardoll, D. M. (1994) Nature 369:357–358; Kawakami, Y., et al., (1994) Proc. Natl. Acad. Sci. U.S.A. 91:3515–3519; Kawakami, Y., et al., (1994) Proc. Natl. Acad. Sci. U.S.A. 91:6458–6462.

DF3/MUC1 (MUC1) is a cell surface glycoprotein that is overexpressed in breast, ovarian, and pancreatic tumors. The major extracellular portion of MUC1 is composed of tandem repeat units of 20 amino acids which comprise immunogenic epitopes. The full length major extracellular MUC1 protein is composed of up to 100 tandem repeat units of 20 amino acids containing 0-glycosylation sites which act as a framework for the formation of a highly glycosylated structure, which is highly immunogenic.

The term "tandem repeat unit" of MUC1 refers to the 20 amino acid repeated sequence of MUC1 (see, e.g., Gendler, S. J., et al (1990) J. Biol. Chem. 265:15286–15293).

(SEQ ID NO:1) GSTAPPAHGVTSAPDTRPAP

There is an abnormal glycosylation pattern found in carcinoma cells making the tumor-derived mucin antigenically distinct from normal mucin. Monoclonal antibodies specific for these peptide epitopes as well as their unique sugar side chains can identify >90% of breast tumors.

See Kufe, D., et al. (1984) Hybridoma 223–32; Taylor-Papadimitriou, J., et al. (1994) Trends Biotechnol. 12:227–33; Fontenot, J. D., et al. (1993) Cancer Res. 53:5386–94; Siddiqui J., et al. (1988) Proc. Natl. Acad. Sci. USA 85:2320–3; Merlo et al. (1989) Cancer Res. 49:6966–6971; and Abe, M., et al. (1989) Biochem Biophys Res Commun 165:644–9.

Accordingly, using the MUC1 tumor-associated antigen (TAA) has been proposed in developing cancer vaccines, particularly against tumors expressing MUC1. Multiple copies of tandem repeats are required for optimal native conformation and immunogenicity (see Fontenot et al., supra). A comparison of synthetic peptides containing 3, 4, or 5.25 tandem repeats of MUC1 revealed that the 5.25-copy version most closely mimicked the native structure of MUC1 and showed the most anti-mucin reactivity (Kotera et al. (1994) Cancer Res. 54:2856–2860). Previous recombinant vaccinia viruses containing the MUC1 gene with numerous tandem repeats were found to be unstable; homologous recombination resulted in deletion of most of the repeats, reducing the efficacy of the vaccine. See, e.g., Acres, R. B., et al. (1993) J. Immunother. 14:136–43; Bu, D., et al. (1993) J. Immunother. 14:127–35; Hareuveni, M., et al. (1990) Proc. Natl. Acad. Sci. USA. 87:9498–502; and Finn O. J. et al. infra.

The use of recombinant vaccinia viruses for anti-tumor immunotherapy has been discussed. (Hu, S. L., Hellstrom, I., and Hellstrom K. E. (1992) in Vaccines: New Approaches to Immunological Problems (R. W. Ellis, ed) pp. 327–343, Butterworth-Heinemann, Boston.) Anti-tumor responses have been elicited using recombinant pox viruses expressing TAAs such as carcinoembryonic antigen (CEA) and prostrate specific antigen (PSA). (Muraro, R., et al., (1985) Cancer Res. 4S:5769–5780); (Kantor, 3., et al. (1992) J. Natl. Cancer Inst. 84:1084–1091); (Robbins, P. F., et al. (1991) Cancer Res. 51:3657–3662) (Kantor, 3., et al. (1992) Cancer Res. 52:6917–6925.) No toxicity with these vectors was observed.

In general, viral vaccines are believed to mediate tumor rejection by activating class I MHC-restricted T-cells, particularly cytotoxic T lymphocytes (CTLs). T-cell activation is often potentiated by providing a suitable immunomodulator, for example a T-cell co-stimulatory factor such as those of the B7 gene family. See e.g., Greenberg, P. D. (1991) in Advances in Immunology, Vol. 49 (Dixon, D. J., ed.), pp. 281–355, Academic Press, Inc., Orlando, Fla.; Fox B. A. et al. (1990) J. Biol. Response Mod. 9:499–511.

It would be useful to have a recombinant pox virus encoding a MUC1 fragment containing a number of tandemly repeated sequences that will generate a cytotoxic T-cell response to MUC1, but which is stable, undergoing minimal excision as a result of homologous recombination in the gene encoding MUC1. It would also be useful to provide the recombinant pox virus in a vaccine format which is capable of potentiating T-cell activity against such tumors, particularly established or pre-existing tumors expressing the MUC1 TAA.

SUMMARY OF THE INVENTION

The present invention relates to recombinant pox viruses encoding a MUC1 fragment, vaccines, and methods of using the recombinant pox viruses and vaccines to generate an immune reaction to MUC1 which can be used to prevent or treat tumors expressing MUC1 TAAs.

The recombinant pox virus of the present invention contains a gene encoding an immunogenic MUC1 fragment of 5 to 25 tandem repeats of the 20 amino acid unit, preferably 7–15 tandem repeats, more preferably about 7–10 tandem repeats, still more preferably about 10 tandem repeats, which when expressed, can vaccinate a mammal against tumors or pre-tumorous cells expressing the MUC1 TAA. This MUC1 gene fragment is stable, maintaining the tandem repeat copy number at around 10 copies.

In some preferred embodiments the DNA segment encoding the tandem repeats is altered from the native pattern by using alternative codons to reduce homology between the repeats. For example, amino acids typically have two or more codons that will encode the same residue (e.g., glycine is encoded by GGT, GGA, GGG, or GGC). By using alternative codons encoding the same amino acid one can further reduce the possibility of undesired recombination events. Additionally, one can also introduce some conservative amino acid changes into different groups of the tandem repeats to further reduce undesired recombination (e.g., glycine/serine, valine/leucine), taking care not to alter a peptide epitope that would reduce its immunogenicity.

The immunogenic "mini-MUC1 fragments" do not undergo significant genetic deletion, thereby improving stability. Moreover, the fragment imparts sufficient immunogenic specificity for MUC1 immunogenicity. The effect can further be enhanced by providing a T-cell co-stimulatory factor such as B7 and/or a cytokine such as interleukin-2 (IL-2), particularly for the treatment of established or pre-existing tumors expressing the MUC1 TAA.

BRIEF DESCRIPTION OF THE DRAWINGS

FIG. 2B: MC38 cells transduced with a retroviral vector containing the mini-MUC1 gene and stained with the DF3 anti-MUC1 antibody. FIG. 2A: Non-transduced MC38 cells.

DETAILED DESCRIPTION OF THE INVENTION

Figure 1:
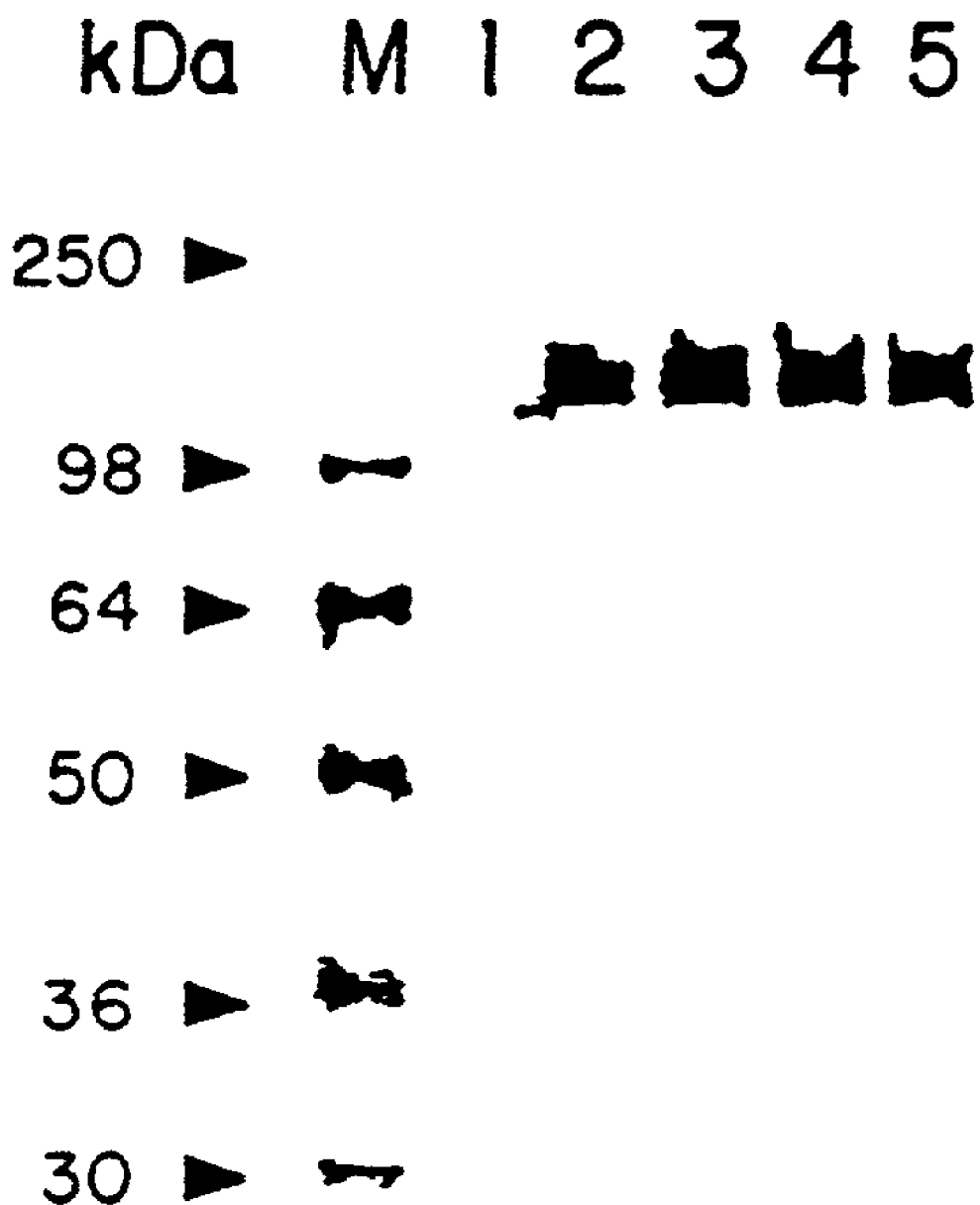
FIG. 1 is a Western blot showing expression of a MUC1 polypeptide, referred to as mini-MUC1 or miMUC1, from rV-MUC1 infected MC38 cells.

Recombinant pox viruses of the present invention encode a mini-MUC1 fragment that can induce an immunogenic response to MUC1, preferably a cytotoxic T cell response, and can thus serve as effective vectors for vaccination against tumors or pre-tumorous cells expressing the MUC1 TAA. Vaccine efficacy can substantially be enhanced by providing an immune modulator such as a T-cell co-stimulatory factor such as B7-1, B7-2 and/or a cytokine such as IL-2. This is preferred in treating established or pre-existing tumors expressing the MUC1 TAA.

A recombinant pox virus of the present invention can be derived from a naturally-occurring or designated wild-type pox virus strain. The pox virus will be a DNA cytoplasmic pox virus which does not integrate into a host cell genome. Exemplary of such pox viruses are suipox (e.g., swine pox), capripox, leporipox, avipox (e.g., fowl pox, canary pox) and orthopox (e.g., vaccinia, ectromelia, rabbit pox). Representative pox viruses can be obtained from the ATTC such as fowlpox (VR-229) and swinepox (VR-363). A particularly preferred pox virus is vaccinia available from the ATCC as the Wyeth Strain (VR-325).

In one preferred embodiment, the recombinant pox viruses of the present invention made from such pox viruses are characterized as being substantially avirulent. That is, it does not cause disease in the desired target cell or tissue. The selected pox virus may have a host range that does not include the target host species, thereby substantially restricting propagation of the virus in the host. For example, swinepox can be used as a pox virus vector in accordance with the present invention when the host is a primate such as a human. Alternatively, a modified strain of the pox virus can be used to confer avirulence in the normal host range of the pox virus.

Exemplary pox viruses for use in accordance with the present invention are suitable orthopox such as vaccinia viruses, avipox such as fowl pox, canary pox and pigeon pox and suipox such as swine pox. Several suitable strains of vaccinia virus are available, e.g., in an attenuated form such as the MVA or Wyeth strain. These vaccinia strains are substantially attenuated in their normal host range (see e.g., Smith, K. A., et al. (1993) *Vaccine* 11:43–53).

A preferred example of a vaccinia virus suitable for making a recombinant vaccinia virus in accordance with the present invention is the Wyeth strain such as the vTBC33 derivative of the Wyeth strain provided in Example 1. A preferred avipox is fowlpox.

An immunogenic MUC1 fragment can be inserted into a suitable pox virus by conventional recombinant techniques to produce the present recombinant pox viruses. For example, as will be explained in more detail in Reference Example 1 and the examples which follow, a DNA donor plasmid vector including a DNA insert encoding an immunogenic MUC1 fragment can be constructed to provide recombination between DNA sequences flanking the insert in the donor plasmid vector and homologous sequences present in the virus. Accordingly, a recombinant virus encoding the immunogenic MUC1 fragment is formed therefrom. Other techniques can be used to make the recombinant virus encoding the immunogenic MUC1 fragment including use of a unique restriction endonuclease site that is naturally present or artificially inserted in the parental viral vector (see e.g., Mackett, et al., *Proc. Natl. Acad. Sci. USA* 79:7415–7419 (1982); and U.S. Pat. No. 5,093,258).

More particularly, the immunogenic MUC1 fragment can be inserted by conventional methods into the DNA donor vector such as those suitable for use in a prokaryote such as *E. coli*. The donor vector will further include viral DNA which is homologous to a segment of pox virus DNA at the site to which insertion of the MUC1 fragment is desired. DNA encoding the immunogenic MUC1 fragment can be inserted into the DNA donor vector adjacent to suitable control elements in the vector such as promoter, enhancer, ribosome binding, and leader sequences. The DNA so inserted into the donor vector is typically positioned to provide flanking viral DNA (e.g., vaccinia HindIIIM fragments) on both ends of the insert. As stated previously, the flanking viral DNA will generally be homologous to a DNA sequence flanking a region of the pox virus DNA to which insertion is desired. Preferably, the homologous flanking viral DNA sequence will be 100% homologous to the region of the pox virus DNA to which insertion is desired. Exemplary DNA donor vectors generally include an origin of replication such as the *E. coli* origin of replication, and a marker such as an antibiotic resistance gene for selection and propagation in a suitable host such as *E. coli*. The resulting DNA donor vector is then propagated by growth within a suitable prokaryotic host cell, isolated and purified if desired.

The DNA donor vector including the immunogenic MUC1 fragment to be inserted into a desired pox virus is generally transfected into a suitable cell culture, e.g., a primate cell line or chick embryo fibroblasts, that is infected with the pox virus. Recombination between homologous DNA in the DNA donor vector and the pox virus genome forms a recombinant pox virus modified by the presence of the immunogenic MUC1 fragment. Preferably, the site of pox virus insertion does not substantially affect the viability of the recombinant pox virus. Viral viability can be readily tested by, e.g., viral plaque assay or a DNA replication assay involving tagging newly synthesized DNA with a detectably-labeled nucleotide (e.g. $^3$H-thymidine). Typically, viral viability will be assessed by comparing the viability of the recombinant pox virus to that of a control pox virus (i.e., no inserted DNA).

As noted above, the immunogenic MUC1 fragment is inserted into a suitable region (insertion region) of a pox virus so that virus viability is not substantially affected. The skilled artisan can readily identify such regions in the pox virus by, for example, randomly testing segments of virus DNA for regions that allow recombinant formation without affecting virus viability of the recombinant. One region that can readily be used and is present in many viruses is the thymidine kinase (TK) gene. For example, it has been found in all pox virus genomes examined (e.g., leporipoxvirus: Upton, et al., *J. Virology*, 60:920 (1986) (shope fibroma virus); capripoxvirus: Gershon, et al., *J. Gen. Virol.*, 70:525 (1989) (Kenya sheep-1); orthopoxvirus: Weir, et al., *J. Virol.*, 46:530 (1983) (vaccinia); Esposito, et al., *Virology*, 135:561(1984) (monkeypox and variola virus); Hruby, et al., *PNAS*, 80:3411(1983) (vaccinia); Kilpatrick, et al., *Virology*, 143:399 (1985) (Yaba monkey tumor virus); avipoxvirus: Binns, et al., *J. Gen. Virol.* 69:1275(1988) (fowlpox); Boyle, et al., *Virology*, 156:355(1987) (fowlpox); Schnitzlein, et al., *J. Virological Methods*, 20:341(1988) (fowlpox, quailpox); entomopox (Lytvyn, et al., *J. Gen. Virol.* 73:3235–3240 (1992)].

In vaccinia, in addition to the TK region, other insertion regions include, for example, HindIII M.

In fowlpox, in addition to the TK region, other insertion regions include, for example, BamHI J [Jenkins, et al., *AIDS Research and Human Retroviruses* 7:991–998 (1991)] the EcoRI-HindIII fragment, BamHI fragment, EcoRV-HindIII fragment, BamHI fragment and the HindIII fragment set forth in EPO Application No. 0 308 220 A1. [Calvert, et al., *J. of Virol.* 67:3069–3076 (1993); Taylor, et al., *Vaccine* 6:497–503 (1988); Spehner, et al., (1990) and Boursnell, et al., *J. Gen. Virol.* 71:621–628 (1990)].

In swinepox preferred insertion sites include the thyrnidine kinase gene region and the HindIIIC region.

In addition to the requirement that the gene be inserted into an insertion region, successful expression of the inserted gene by the modified poxvirus requires the presence of a promoter operably linked to the desired gene, i.e., in the proper relationship to the inserted gene. The promoter must be placed so that it is located upstream from the gene to be expressed. Promoters are well known in the art and can readily be selected depending on the host and the cell type you wish to target. For example in poxviruses, pox viral promoters should be used, such as the vaccinia 7.5K, or 40K or fowlpox Cl. Artificial pox promoter constructs containing appropriate promoter sequences can also be used. Enhancer elements can also be used in combination to increase the level of expression. Furthermore, the use of inducible promoters, which are also well known in the art, are preferred in some embodiments.

For example, it is possible to make a DNA vector construct in which the promoter is modulated by an external factor or cue, and in turn to control the level of polypeptide being produced by the vectors by activating that external factor or cue. For example, heat shock proteins are proteins encoded by genes in which the promoter is regulated by temperature. The promoter of the gene which encodes the metal-containing protein metallothionine is responsive to Cd+ ions. Incorporation of this promoter or another promoter influenced by external cues also makes it possible to regulate the production of the proteins.

The pox vectors of the present invention contain a DNA fragment encoding a MUC1 fragment, sometimes referred to as mini-MUC. The MUC1 gene fragment will encode a sufficient portion of MUC1 to generate an immune reaction to MUC1, but does not undergo extensive excision as a result of homologous recombination. Preferably, the fragment is approximately 5 to 25 MUC1 tandem repeat units, more preferably between approximately 7 to 15 MUC1 tandem repeat units, and most preferably about 7 to 12 MUC1 tandem repeat units. An especially preferred immunogenic MUC1 fragment is about 10 MUC1 tandem repeat units. Preferred fragments have the human MUC1 DNA sequence. A preferred MUC1 DNA sequence is the human MUC1 cDNA sequence having the repeat units disclosed, e.g., by Gendler et al. supra. While the sequence reported by Merlo et al., supra, is 10 MUC1 tandem repeat units, a sample based on this was only about 7 tandem repeat units. This sample is more fully described in the examples.

In some preferred embodiments the DNA segment encoding the tandem repeats is altered from the native pattern in such a manner as to reduce duplications of the codons. For example, amino acids typically have two or more codons that will encode the same residue (e.g., glycine is encoded by GGT, GGA, GGG, or GGC). By using other codons encoding the same amino acid one can further reduce the possibility of undesired recombination events. Additionally, one can also introduce some conservative amino acid changes into different groups of the tandem repeats to further reduce undesired recombination (e.g., glycine/serine, valine/leucine), taking care not to alter a peptide epitope that would reduce its immunogenicity.

Preferably, the 60 bp tandem repeat sequence can be altered to minimize nucleotide homology without changing the amino acid sequence. For example the first tandem repeat in miMUC1 can be left unaltered as follows:

| 1 | 2 | 3 | 4 | 5 | 6 | 7 | 8 | 9 | 10 |
|---|---|---|---|---|---|---|---|---|---|
| GGC | TCC | ACC | GCC | CCC | CCA | GCC | CAC | GGT | GTC |
| G | S | T | A | P | P | A | H | G | V |

| 11 | 12 | 13 | 14 | 15 | 16 | 17 | 18 | 19 | 20 |
|---|---|---|---|---|---|---|---|---|---|
| ACC | TCG | GCC | CCG | GAC | ACC | AGG | CCG | GCC | CCG |
| T | S | A | P | D | T | R | P | A | P |

*(SEQ ID NO:2)

The second, third, and fourth tandem repeats can then be altered in the third base of threonine codons 3, 11 and 16 using ACG, ACT, and ACA, respectively. These repeats can also be altered in alanine codons 4, 7, 13, and 19, using GCG, GCA, and GCT respectively. Similar third-base alterations can be incorporated at numerous codons in each of the tandem repeats to minimize homologous recombination among the repeats. One example of MUC1 repeat sequences using wobbled codons to minimize homology while retaining repeated amino acid sequence is set forth below in Table A.

For parenteral administration, the recombinant vectors will typically be injected in a sterile aqueous or non-aqueous solution, suspension or emulsion in association with a pharmaceutically-acceptable carrier such as physiological saline.

TABLE A

| | | | | | | | | | | | | | | | | | | |
|---|---|---|---|---|---|---|---|---|---|---|---|---|---|---|---|---|---|---|
| R1 | GGC | TCC | ACC | GCC | CCC | CCA | GCC | CAC | GGT | GTC | ACC | TCG | GCC | CCG | GAC | ACC | AGG | CCG GCC CCG | (SEQ ID NO:2) |
| R2 | GGC | AGT | ACT | GCA | CCA | CCG | GCA | CAT | GGC | GTA | ACA | TCA | GCA | CCT | GAT | ACA | AGA | CCT GCA CCT | (SEQ ID NO:4) |
| R3 | GGA | TCC | ACC | GCG | CCG | CCT | GCG | CAC | GGA | GTG | ACG | TCG | GCG | CCC | GAC | ACG | CGC | CCC GCT CCC | (SEQ ID NO:5) |
| R4 | GGG | TCA | ACA | GCT | CCT | CCC | GCT | CAT | GGG | GTT | ACT | TCT | GCT | CCA | GAT | ACT | CGC | CCA GCT CCA | (SEQ ID NO:6) |
| R5 | GGT | TCG | ACG | GCC | CCC | CCT | GCT | CAC | GGT | GTA | ACA | TCC | GCC | CCG | GAT | ACC | AGA | CCG GCC CCT | (SEQ ID NO:7) |
| R6 | GGC | AGC | ACC | GCA | CCG | CCC | GCA | CAC | GGG | GTC | ACA | AGC | GCG | CCA | GAC | ACT | CGA | CCT GCG CCA | (SEQ ID NO:8) |
| R7 | GGA | AGT | ACC | GCT | CCA | CCT | GCA | CAC | GGG | GTC | ACA | AGC | GCG | CCA | GAC | ACT | CGA | CCT GCG CCA | (SEQ ID NO:9) |
| R8 | GGG | TCG | ACT | GCC | CCT | CCG | GCG | CAT | GGT | GTG | ACC | TCA | GCT | CCT | GAC | ACA | AGG | CCA GCC CCA | (SEQ ID NO:10) |
| R9 | GGT | TCA | ACG | GCA | CCT | CCA | GCA | CAC | GGA | GTC | ACG | TCT | GCA | CCC | GAC | ACC | CGT | CCA GCT CCG | (SEQ ID NO:11) |
| R10 | GGT | AGT | ACA | GCG | CCA | CCC | GCA | CAT | GGC | GTC | ACG | AGC | GCT | CCG | GAT | ACG | AGA | CCG GCG CCT | (SEQ ID NO:12) |
| | G | S | T | A | P | P | A | H | G | V | T | S | A | P | D | T | R | P A P | (SED ID NO:1) |

One can use the various sequences in any combination. Further, one does not need to use all 10 repeats.

Nucleotide homology can also be reduced by introducing changes to the amino acid sequence, preferably conservative amino acid substitutions into some of the tandem repeats. Immunogenic epitopes such as (SEQ ID NO:3) PDTRPAP would preferably be left intact, but valine codon 10 could be changed to leucine codons CTT, CTC, CTA, and CTG in different repeats.

An immunogenic MUC1 fragment according to the invention can be made by a variety of conventional methods. For example, the fragment can be made by cloning a desired portion of the full-length human MUC1 DNA sequence (see e.g., Merlo, et al., supra; and Abe, M., et al., supra). Restriction enzymes can be used to cleave the desired fragment. The immunogenic MUC1 DNA fragment can also be prepared by amplification by the Polymerase Chain Reaction (i.e., PCR). Use of cloning and PCR amplification techniques to make an immunogenic MUC1 fragment is disclosed in Example 1 which follows.

An immunogenic mini-MUC1 fragment in accordance with the present invention can be inserted into a suitable pox virus to produce a recombinant pox virus which encodes the intact fragment and is reasonably stable. Expression of the immunogenic MUC1 fragment can be readily determined by several methods, including assaying samples of a suitable target cell or tissue by SDS-PAGE gel electrophoresis followed by Coomassie blue or silver staining; Western blot using DF3 antibody, or other suitable immunological technique such as ELISA.

Live recombinant viruses expressing an immunogenic cell encoded tumor associated antigen can be used to induce an immune response against tumor cells which express the protein. These recombinant viruses may be administered by scarification, as was conventionally done for small pox vaccination, or by other routes appropriate to the recombinant virus used. These may include among others, intramuscular, intradermal, subcutaneous, and intravenous routes. Vaccination of a host organism with live recombinant vaccinia virus is followed by replication of the virus within the host.

Kits containing the vector and the means for injection can be used. The kit preferably contains instructions describing how to use the vector. In one embodiment, the kit contains a vector modified to include an immunomodulator or a separate vector containing the immunomodulator as described below. In addition the kit can contain an adjuvant.

A specific immune response to a tumor associated antigen can be generated by administering between about $10^5$–$10^9$ pfu of the recombinant pox virus, constructed as discussed above to a host; more preferably one uses $\geq 10^7$ pfu. The preferred host is a human. At least one interval thereafter, which is preferably one to three months later, the immune response is boosted by administering additional antigen to the host. More preferably there is at least a second "boost" preferably at least one to three months after the first boost, more preferably 6–12 months after the first boost. The boosting antigen may be administered using the same pox virus vector, or as a whole protein, an immunogenic peptide fraction of the protein, another recombinant viral vector, or DNA encoding the protein or peptide. Preferably, different pox viral vectors are used. For example, vaccinia may be followed by an avipox such as fowlpox, or vice versa. Cytokines, e.g., IL-2, IL-6, IL-12, IL-15, or co-stimulatory molecules, e.g., B7.1, B7.2, may be used as biologic adjuvants. The cytokines can be administered systemically to the host. Either cytokines or co-stimulatory molecules can be co-administered via co-insertion of the genes encoding the molecules into the recombinant pox vector or a second recombinant poxvirus which is admixed with the recombinant poxvirus expressing the TAA.

Adjuvants include, for example, RIBI Detox (Ribi Immunochemical), QS21 (Aquila), incomplete Freund's adjuvant or many others.

Alternatively, it will sometimes be useful to use a recombinant pox virus encoding the immunogenic MUC1 fragment which has been modified to include an immunomodulator, for example, DNA encoding a T-cell co-stimulatory factor and/or a cytokine such as interleukin (IL) (e.g., IL-2, IL-4, IL-10, IL-12), an interferon (IFN) (e.g., IFN-γ), granulocyte macrophage colony stimulating factor (GM-CSF) or an accessory molecule (e.g. ICAM-1). The construction of such multivalent vectors such as pox viral vectors is within the level of skill in the art based upon the present disclosure. In some cases, co-expression of the immunomodulatory agent such as the T-cell co-stimulatory factor and the immunogenic fragment of MUC1 by multiple vectors may be desirable. It may be desirable to administer a substantially pure preparation of, e.g., the immunomodulator to boost vaccine efficacy.

In preferred embodiments after initial administrations of the viral vector by one pox a different pox virus, preferably from a different pox family will be used for the following administrations (i.e. boosts). For example, initial administrations by vaccinia or avipox would preferably be followed by boosts from an avipox or vaccina, respectively, or by a suipox.

Although initially generally less preferred in most cases, it may be desirable to use another DNA or RNA virus or vector to insert an immunogenic MUC1 DNA fragment into a subject host. Such an approach may be useful where multiple boosts are used and the subject is at risk of developing an antigenic reaction to the host pox vector. Exemplary of such vectors are DNA or RNA viruses such as retroviruses, adenoviruses, herpes viruses or DNA-based vectors (see generally, Cepko et al., Cell 37:1053–1062 (1984); Morin et al., Proc. Natl. Acad. Sci. USA 84:4626–4630 (1987); Lowe et al., Proc. Natl. Acad. Sci. USA, 84:3896–3900 (1987); Panicali & Paoletti, Proc. Natl. Acad. Sci. USA, 79:4927–4931(1982); Mackett et al., Proc. Natl. Acad. Sci. USA, 79:7415–7419 (1982)). In an alternative embodiment, one would prime first with a non-pox viral vector expressing mini-MUC1, or a DNA segment encoding mini-MUC1, followed by boosting, wherein at least one boost involves the use of pox vectors.

Further contemplated uses of the recombinant pox viruses disclosed herein include use in the production of antibodies, particularly monoclonal antibodies that are capable of specifically binding the immunogenic MUC1 fragments. More specifically, it can be desirable to produce the antibodies, e.g., to detect mucin glycosylation in tumor and pre-tumorous cells in vitro and in vivo. The antibodies may be prepared by a variety of standard methods well-known to those skilled in the art. For example, cells expressing an immunogenic MUC1 fragment can be administered to an animal to induce production of polyclonal antibodies. Alternatively, monoclonal antibodies which specifically bind an immunogenic MUC1 fragment can be prepared using hybridoma technology (see, e.g., Kohler et al., Nature 256: 495 (1975); Hammerling et al., In Monoclonal Antibodies and T Cell Hybridomas, Elsevier, N.Y. (1981)).

Cytotoxic T-cells specific for an immunogenic MUC1 fragment can be established from peripheral blood mononuclear cells (PBMC) obtained from a host immunized as discussed above. For example, PBMC can be separated by using Lymphocyte Separation Medium gradient (Organon Teknika, Durham, N.C., USA) as previously described Boyum, et al., Scand J. Clin Lab Invest 21: 77–80 (1968). Washed PBMC are resuspended in a complete medium, for example, RPMI 1640 (GIBCO) supplemented with 10% pool human AB serum (Pel-Freeze Clinical System, Brown Dear, Wis., USA), 2 mM glutamine, 100 U/ml penicillin and 100 µg/ml of streptomycin (GIBCO). PBMC at a concentration of about $2\times10^5$ cells in complete medium in a volume of, for example, 100 µl are added into each well of a 96-well flat-bottom assay plate (Costar, Cambridge, Mass., USA). The immunogenic MUC1 fragment can be added to the cultures in a final concentration of about 50 µg/ml and incubated at 37° C. in a humidified atmosphere containing 5% $CO_2$ for 5 days. After removal of the media containing the fragment, the cultures are provided with fresh human IL-2 (10 U/ml) after 5 days and replenished with IL-2 containing medium every 3 days. Primary cultures are restimulated with the immunogenic MUC1 fragment (50 µg/ml) on day 16. $5\times10^5$ irradiated (4,000 rad) autologous PBMC are added in a volume of about 50 µl complete medium as antigen-presenting cells (APC). About five days later, the cultures are provided with human IL-2 containing medium as described previously. Cells are restimulated for 5 days at intervals of 16 days.

The cytotoxic T-cells can be cultured in accordance with known methods and then injected back into the host by a variety of means. Generally, between $1\times10^5$ and $2\times10^{11}$ cytotoxic T-cells per infusion are administered in, for example, one to three infusions of 200 to 250 ml each over a period of 30 to 60 minutes. After the completion of the infusions, the patient may be treated with recombinant interleukin-2 with a dose of 720,000 IU per kilogram of body weight intravenously every eight hours; some doses can be omitted depending on the patient's tolerance for the drug. In addition, after infusion, additional recombinant pox virus or immunogenic MUC1 fragment containing T-cell eliciting epitope(s) may be administered to the patient to further expand the T-cell number. The antigen or epitope may be formulated with an adjuvant and/or may be in a liposomal formulation.

The cytotoxic T-cells can also be modified by introduction of a viral vector containing a DNA encoding TNF and reintroduced into a host in an effort to enhance the antitumor activity of the cells.

REFERENCE EXAMPLE 1

Pox Viruses

A number of pox viruses have been developed as live viral vectors for the expression of heterologous proteins. Representative vaccinia virus strains such as Wyeth and MVA have been disclosed previously. (Cepko et al., Cell 37:1053–1062 (1984); Morin et al., Proc. Natl. Acad. Sci. USA 84:4626–4630 (1987); Lowe et al., Proc. Natl. Acad. Sci. USA, 84:3896–3900 (1987); Panicali & Paoletti, Proc. Natl. Acad. Sci. USA, 79:4927–4931(1982); Mackett et al., Proc. Natl. Acad. Sci. USA, 79:7415–7419 (1982)). Representative fowlpox and swinepox virus are available through the ATCC under accession numbers VR-229 and VR-363, respectively. The Wyeth strain of vaccinia is available through the ATCC under accession number VR-325.

DNA Vectors for In Vivo Recombination with a Parent Virus

Genes that code for desired carcinoma associated antigens are inserted into the genome of a pox virus in such a manner as to allow them to be expressed by that virus along with the expression of the normal complement of parent virus proteins. This can be accomplished by first constructing a DNA donor vector for in vivo recombination with a pox virus.

In general, the DNA donor vector contains the following elements:

(i) a prokaryotic origin of replication, so that the vector may be amplified in a prokaryotic host;

(ii) a gene encoding a marker which allows selection of prokaryotic host cells that contain the vector (e.g., a gene encoding antibiotic resistance);

(iii) at least one gene encoding a desired protein located adjacent to a transcriptional promoter capable of directing the expression of the gene; and (iv) DNA sequences homologous to the region of the parent virus genome where the foreign gene(s) will be inserted, flanking the construct of element (iii).

Methods for constructing donor plasmids for the introduction of multiple foreign genes into pox virus are described in WO91/19803, the techniques of which are incorporated herein by reference. In general, all DNA fragments for construction of the donor vector, including fragments containing transcriptional promoters and fragments containing sequences homologous to the region of the parent virus genome into which foreign genes are to be inserted, can be obtained from genomic DNA or cloned DNA fragments. The donor plasmids can be mono-, di-, or multivalent (i.e., can contain one or more inserted foreign gene sequences).

The donor vector preferably contains an additional gene which encodes a marker which will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., *J. Virol.*, 62:1046 (1988); Falkner and Moss., *J. Virol.*, 62:1849 (1988); Franke et al., *Mol. Cell. Biol.*, 5:1918 (1985), as well as genes such as the *E. coli* lacZ gene, that permit identification of recombinant viral plaques by colorimetric assay (Panicali et al., *Gene*, 47:193–199 (1986)).

Integration of Foreign DNA Sequences into the Viral Genome and Isolation of Recombinants Homologous recombination between donor plasmid DNA and viral DNA in an infected cell results in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo dermal (CED) cells, HuTK143 (human) cells, and CV-1 and BSC-40 (both monkey kidney) cells. Infection of cells with pox virus and transfection of these cells with plasmid vectors is accomplished by techniques standard in the art (Panicali and Paoletti, U.S. Pat. No. 4,603,112, WO89/03429). Alternatively, the donor DNA can be directly ligated into the parental virus genome at a unique restriction site (Scheiflinger, et al. (1992) *Proc. Natl. Acad. Sci.* (USA) 89:9977–9981).

Following in vivo recombination or ligation, recombinant viral progeny can be identified by one of several techniques. For example, if the DNA donor vector is designed to insert foreign genes into the parent virus thymidine kinase (TK) gene, viruses containing integrated DNA will be TK⁻ and can be selected on this basis (Mackett et al., *Proc. Natl. Acad. Sci. USA*, 79:7415 (1982)). Alternatively, co-integration of a gene encoding a marker or indicator gene with the foreign gene(s) of interest, as described above, can be used to identify recombinant progeny. One preferred indicator gene is the *E. coli* lacZ gene: recombinant viruses expressing β-galactosidase can be selected using a chromogenic substrate for the enzyme (Panicali et al., Gene, 47:193 (1986)).

Characterizing the Viral Antigens Expressed by Recombinant Viruses

Once a recombinant virus has been identified, a variety of methods can be used to assay the expression of the polypeptide encoded by the inserted gene. These methods include black plaque assay (an in situ enzyme immunoassay performed on viral plaques), Western blot analysis, radioimmunoprecipitation (RIPA), enzyme immunoassay (EIA), or functional assay such as CTL assay.

EXAMPLE 1

Construction of Recombinant Vaccinia Virus Encoding MUC1 Gene Sequences

A. Mini-MUC1 Gene Vector

The human DF3/MUC1 cDNA was constructed from two cloned cDNA segments [Merlo, et al., supra; Abe, M. et al., surpa]. A 1.8 kb EcoRI fragment of MUC1 cDNA reported as containing 10 tandem repeats and its 3' unique sequence was inserted into Bluescript™ plasmid (Stratagene, La Jolla, Calif.) at the EcoRI site and designated pBs-MUC1. The 5' end of the MUC1 gene was generated from another MUC1 clone by PCR using MUC1 specific primers. The 200 base pair amplification fragment was inserted into pBs-MUC1 at the HindIII and HindIII sites creating pBS-miMUC1 containing the "mini" MUC1 gene (sometimes referred to herein as "miMUC1"). However, DNA sequence analysis of the miMUC1 gene confirmed that this gene contained the appropriate signal and start site, but not 10 tandem repeats. Instead it contained 7 repeats that showed some variation. The DNA sequence of the repeated portion of the miMUC1 gene is set forth below in Table B.

The deduced amino acid sequence of the repeat region predicted from nucleotide sequence analysis of MUC1 gene is set forth below in Table C.

Moreover, the 3' coding sequence actually differs from that reported by Merlo, supra, but conforms to the 3' sequence reported by Gendler, supra. The entire coding sequence of the miniMUC1 gene is shown in Table D.

TABLE B

| R1 | | GGC TCC ACC GCC CCC CCA GCC CAC GGT GTC ACC TCG CCG GCC GAC | (SEQ ID NO:2) |
|---|---|---|---|
| | | ACC AGG CCG GCC CCG | |
| R2 | | GGC TCC ACC GCC CCC CCA GCC CAC GGT GTC ACC TCG CCG CCG GAC | (SEQ ID NO:2) |
| | | ACC AGG CCG GCC CCG | |
| R3 | | GGC TCC ACC GCC CCC CCA GCC CAC GGT GTC ACC TCG CCG CCG GAC | (SEQ ID NO:2) |
| | | ACC AGG CCG GCC CCG | |
| R4 | | GGC TCC ACC GCC CCC CCA GCC CAC GGT GTC ACC TCG CCG CCG GAC | (SEQ ID NO:2) |
| | | ACC AGG CCG GCC CCG | |
| R5 | GGC TCC ACC GCA CCC CCA GCC CAC GGT GTC ACC TCG CCC CCG GAC ACC AGG CGG GCC CCG GGC | TCC ACC CCG GCC CCG | (SEQ ID NO:13) |
| R6 | | GGC TCC ACC GCC CCC CCA GCC CAT GGT GTC ACC TCG GCC CCG GAC | (SEQ ID NO:14) |
| | | ACC AGG CCC GCC TTG | |
| R7 | | GGC TCC ACC GCC CCT CCA GTC CAC AAT GTC ACC TCG GCC | (SEQ ID NO:15) |

TABLE C

| | | |
|---|---|---|
| Repeat 1 | G S T A P P A H G V T S A P D T R P A P | (SEQ ID NO:1) |
| Repeat 2 | G S T A P P A H G V T S A P D T R P A P | (SEQ ID NO:1) |
| Repeat 3 | G S T A P P A H G V T S A P D T R P A P | (SEQ ID NO:1) |
| Repeat 4 | G S T A P P A H G V T S A P D T R P A P | (SEQ ID NO:16) |
| Repeat 5: G S T P A P | G S T A P P A H G V T S A P D T R P A P | (SEQ ID NO:1) |
| Repeat 6: | G S T A P P A H G V T S A P D T R P A P | (SEQ ID NO:17) |
| Repeat 7: | G S T A P P V H N V T S A | (SEQ ID NO:18) |

TABLE D (SEQ ID NO:19)

```
ATGACACCGGGCACCCAGTCTCCTTTCTTCCTGCTGCTGCTCCTCACAGTGCTT
 M  T  P  G  T  Q  S  P  F  F  L  L  L  L  T  V  L

ACAGCTACCACAGCCCCTAAACCCGCAACAGTTGTTACGGGTTCTGGTCATGCA
 T  A  T  T  A  P  K  P  A  T  V  V  T  G  S  G  H  A

AGCTCTACCCCAGGTGGAGAAAAGGAGACTTCGGCTACCCAGAGAAGTTCAGTG
 S  S  T  P  G  G  E  K  E  T  S  A  T  Q  R  S  S  V

CCCAGCTCTACTGAGAAGAATGCTGTGAGTATGACAAGCTTGATATCGAATTCC
 P  S  S  T  E  K  N  A  V  S  M  T  S  L  I  S  N  S

GGTGTCCGGGGCTCCACCGCCCCCCCAGCCCACGGTGTCACCTCGGCCCCGGAC
 G  V  R  G  S  T  A  P  P  A  H  G  V  T  S  A  P  D

ACCAGGCCGGCCCCGGGCTCCACCGCCCCCCCAGCCCACGGTGTCACCTCGGCC
 T  R  P  A  P  G  S  T  A  P  P  A  H  G  V  T  S  A

CCGGACACCAGGCCGGCCCCGGGCTCCACCGCCCCCCCAGCCCACGGTGTCACC
 P  D  T  R  P  A  P  G  S  T  A  P  P  A  H  G  V  T

TCGGCCCCGGACACCAGGCCGGCCCCGGGCTCCACCGCACCCCCAGCCCACGGT
 S  A  P  D  T  R  P  A  P  G  S  T  A  P  P  A  H  G

GTCACCTCGGCCCCGGACACCAGGCGGGCCCCGGGCTCCACCCCGGCCCCGGGC
 V  T  S  A  P  D  T  R  R  A  P  G  S  T  P  A  P  G

TCCACCGCCCCCCCAGCCCACGGTGTCACCTCGGCCCCGGACACCAGGCCGGCC
 S  T  A  P  P  A  H  G  V  T  S  A  P  D  T  R  P  A

CCGGGCTCCACCGCCCCCCCAGCCCATGGTGTCACCTCGGCCCCGGACAACAGG
 P  G  S  T  A  P  P  A  H  G  V  T  S  A  P  D  N  R

CCCGCCTTGGGCTCCACCGCCCCTCCAGTCCACAATGTCACCTCGGCCTCAGGC
 P  A  L  G  S  T  A  P  P  V  H  N  V  T  S  A  S  G

TCTGCATCAGGCTCAGCTTCTACTCTGGTGCACAACGGCACCTCTGCCAGGGCT
 S  A  S  G  S  A  S  T  L  V  H  N  G  T  S  A  R  A

ACCACAACCCCAGCCAGCAAGAGCACTCCATTCTCAATTCCCAGCCACCACTCT
 T  T  T  P  A  S  K  S  T  P  F  S  I  P  S  H  H  S

GATACTCCTACCACCCTTGCCAGCCATAGCACCAAGACTGATGCCAGTAGCACT
 D  T  P  T  T  L  A  S  H  S  T  K  T  D  A  S  S  T

CACCATAGCACGGTACCTCCTCTCACCTCCTCCAATCACAGCACTTCTCCCCAG
 H  H  S  T  V  P  P  L  T  S  S  N  H  S  T  S  P  Q

TTGTCTACTGGGGTCTCTTTCTTTTTCCTGTCTTTTCACATTTCAAACCTCCAG
 L  S  T  G  V  S  F  F  F  L  S  F  H  I  S  N  L  Q

TTTCCTTCCTCTCTCGAAGATCCCAGCACCGACTACTACCAAGAGCTGCAGAGA
 F  P  S  S  L  E  D  P  S  T  D  Y  Y  Q  E  L  Q  R

GACATTTCTCAAATGTTTTTGCAGATTTATAAACAAGGGGGTTTTCTGGGCCTC
 D  I  S  Q  M  F  L  Q  I  Y  K  Q  G  G  F  L  G  L
```

TABLE D-continued (SEQ ID NO:19)

```
TCCAATATTAAGTTCAGGCCAGGATCTGTGCTGGTACAATTGACTCTGGCCTTC
  S  N  I  K  F  R  P  G  S  V  L  V  Q  L  T  L  A  F

CGAGAAGGTACCATCAATGTCCACGACGTGGAGACACAGTTCAATCAGTATAAA
  R  E  G  T  I  N  V  H  D  V  E  T  Q  F  N  Q  Y  K

ACGGAAGCAGCCTCTCGATATAACCTGACGATCCCAGACGTCAGCGTGAGTGAT
  T  E  A  A  S  R  Y  N  L  T  I  P  D  V  S  V  S  D

GTGCCATTTCCTTTCTCTGCCCAGTCTGGGGCTGGGGTGCCAGGCTGGGGCATC
  V  P  F  P  F  S  A  Q  S  G  A  G  V  P  G  W  G  I

GCGCTGCTCCTGCTGGTCTGTGTTCTGTTGCGCTGGCCATTGTCTATCTCATT
  A  L  L  L  L  V  C  V  L  V  A  L  A  I  V  Y  L  I

GCCTTGGCTGTCTGTCAGTGCCGCCGAAAGAACTACGGGCAGCTGGACATCTTT
  A  L  A  V  C  Q  C  R  R  K  N  Y  G  Q  L  D  I  F

CCAGCCCGGGATACCTACCATCCTATGAGCGAGTACCCCACCTACCACACCCAT
  P  A  R  D  T  Y  H  P  M  S  E  Y  P  T  Y  H  T  H

GGGCGCTATGTCCCCCCTAGCAGTACCGATCGTAGCCCCTATGAGAAGGTTTCT
  G  R  Y  V  P  P  S  S  T  D  R  S  P  Y  E  K  V  S

GCAGGTAATGGTGGCAGCAGCCTCTCTTACACAAACCCAGCAGTGGCAGCCACT
  A  G  N  G  G  S  S  L  S  Y  T  N  P  A  V  A  A  T

TCTGCCAACTTGTAG
  S  A  N  L
```

B. Recombinant Vaccinia Virus

The miMUC1 gene described above was inserted 3' to the vaccinia 40K early/late promoter and flanked by sequences from the Hind III M region of the vaccinia genome. The resulting plasmid, designated pT2041, contained the miMUC1 gene under the control of the vaccinia virus 40K early/late promoter flanked by DNA sequences from the Hind III M region of the vaccinia genome. These flanking sequences included the vaccinia K1L host range gene required for growth of vaccinia virus on rabbit kidney RK13 cells (ATCC CCL37). A plaque-purified derivative of the Wyeth strain of vaccinia was used as the parental virus (designated vTBC33), lacked a functional K1L gene and thus could not efficiently replicate on RK13 cells. See e.g., Gritz, L., et al. (1990) *J. Virol.* 64:5948–57; Gillard, S., et al. (1986) *Proc. Natl. Acad. Sci. USA.* 83.5573–7; and Smith, K A., et al., supra.

Generation of recombinant vaccinia virus was accomplished via homologous recombination between vaccinia sequences in the vTBC33 genome and the corresponding sequences in pT2041 in vaccinia-infected RK13 cells transfected with pT2041. Recombinant virus, designated vT46 (rV-MUC1), was selected by growth on RK13 cells (ATCC CCL37). Virus stocks were prepared by clarifying infected RK13 cell lysates followed by centrifugation through a 36% sucrose cushion.

The selection and screening of rV-MUC1 was done by growth in RK13 cells. The recombinant vaccinia rV-MUC1 was isolated as a single recombinant clone and purified by two rounds of plaque purification. The miMUC1 gene insertion into the vaccinia virus genome HindIII site by homologous recombination was confirmed by Southern analysis with $^{32}$P radiolabeled miMUC1 gene as a probe. The Southern analysis indicated that the vaccinia virus had not deleted any portions of the gene, in contrast to the deletions reported with full-length MUC1 genes (see Bu, D., et al. supra).

A plasmid similar to pT2041 was constructed that contained the lacZ gene in addition to the mini-MUC1 gene; this plasmid was designated pT2068. The plasmid DNA pT2068 was deposited with the American Type Culture Collection (ATCC), 12301 Parklawn Drive, Rockville, Md. 20852, under the conditions of the "Budapest Treaty on the International Recognition of the Report of Microorganisms for the Purpose of Patent Procedure." The deposit was given ATCC Designation 97893. If the culture dies or is destroyed during the effective term, it will be replaced if a patent issues. If a patent issues, the strain will be maintained for 30 years from the date of deposit, or five years after the most recent request, whichever is longer.

PT2068 was used to construct a recombinant vaccinia virus containing mini-MUC1 using a colorimetric screen for β-gal.

A recombinant vaccinia virus strain expressing the human co-stimulatory molecule B7-1 (designated rV-B7) has been disclosed. The virus was grown in spinner cultures of HeLa cells, directly pelleted by centrifugation, and purified over 20%–40% sucrose gradients (Hodge, J. W., et al. (1994) *Cancer Res.* 54:5552–5; Earl, P. L., et al. (1993) *Generation of recombinant vaccinia viruses*, Vol. 2, Suppl. 21, 16.17.1–16.18.10. New York: John Wiley & Sons).

EXAMPLE 2

Characterization of Recombinant Vaccinia Virus With miMUC1 Insert

A. Southern Blot Hybridization Analysis

BSC-1 cells (ATCC CC 126) were infected at an MOI of 10 with either miMUC1 recombinant vaccinia virus (designated rV-MUC1) or V-Wyeth. The viral DNA extraction, restriction endonuclease digestion and Southern blotting was performed as previously described (see e.g., Kaufman, H., et al. (1991) *Int. J. Cancer.* 48:900–7). The results indicated that the miMUC1 gene was stably inserted into the HindIII region of the vaccinia genome.

B. Western Analysis of Protein Expression and Stability

Parallel confluent BSC-1 cells were infected with either parental wild type vaccinia virus (V-Wyeth), or rV-MUC1 at an MOI of 5 in Dulbecco's modified Eagle's medium containing 2.5% FBS. After an overnight infection, cells in one plate were scraped and lysed in hypotonic lysis buffer (100 mM Tris-HCI pH 8.0, 100 mM NaCI, 0.5% NP-40, and 0.2 mM PMSF). The infected cells in the corresponding parallel plate were scraped and high titer virus preparations were derived as previously described (Earl, P. L., et al. (1993) *Generation of recombinant vaccinia viruses*, Vol. 2, Supplement 21, 16.17.1–16.18.10. New York: John Wiley & Sons). The resulting virus was used to infect parallel confluent BSC-1 cells as before. This cycle was repeated to generate protein extracts from cells infected with rV-MUC1 that had gone through 2, 3, 4, and 5 passages of viral replication. Cell lysates were electrophoresed on an SDS-10% acrylamide gel. Proteins were electroblotted onto nitrocellulose, blocked, incubated with DF3 antibody (Kufe, D., et al. supra) for 4 hours at room temperature, washed and incubated with goat anti-mouse phosphatase labeled secondary antibody (Kirkegaard and Perry, Gaithersburg, Md.) and developed according to the manufacturer's instructions.

Stable expression of MUC1 after 2, 3, 4 or 5 passages of viral replication of rV-MUC1 was confirmed by Western analysis (FIG. 1). Incubation of protein extracted from rV-MUC1 infected cells from passage 2 (FIG. 1, lane 2) with the monoclonal antibody DF3 revealed a broad 150–175 kD band. Similarly, incubation of protein extracted from cells infected with viral passages 3, 4, and 5 with DF3 (lanes 3, 4, and 5) revealed identical bands ranging from 150–175 kD. Lane 1 contains purified MUC1 protein of approximately 3OOkD. This finding is consistent with reports indicating the apparent molecular mass of these glycoproteins, which appear heterogeneous as a result of 0-linked glycosylation in the tandem repeats (Sekine, H., et al. (1985) *J. Immunol.* 135:3610–5). Uninfected or V-Wyeth infected cells were negative for the expression of MUC1 by Western blot using DF3 MAb.

EXAMPLE 3

Construction and Characterization of Recombinant Vaccinia Virus Containing MUC1 and B7.1

The miMUC1 gene and the human B7.1 gene were each ligated to vaccinia promoters. The promoter-gene cassettes were then inserted into a plasmid vector containing the *E. coli* lacZ gene flanked by DNA sequences from the HindIII M region of the vaccinia genome. The resulting plasmid, designated pT2043, contains the B7.1 gene under the control of the vaccinia virus 30K promoter (located at the HindIII M insertion site; Perkus et al. (1985) Science 229: 981–984), the MUC1 gene under the control of the vaccinia virus 40K early/late promoter (Gritz et al., supra), and the lacZ gene under the control of the fowlpox Cl promoter (Jenkins et al., (1991) AIDS Res. Human Retrovirus 7:991–998), all flanked by DNA sequences from the HindIII M region of the vaccinia genome. A plaque-purified derivative of the Wyeth strain of vaccinia was used as the parental virus in the construction of recombinant vaccinia virus. The generation of recombinant vaccinia virus was accomplished via homologous recombination between vaccinia sequences in the Wyeth vaccinia genome and the corresponding sequences in pT2043 in vaccinia-infected $RK_{13}$ cells transfected with pT2043. Recombinant virus, designated vT2043, was identified using a chromogenic substrate for β-galactosidase (Bluo-Gal™). Viral plaques expressing lacZ appeared blue against a clear background. Positive plaques were picked from the cell monolayer and their progeny were further propagated. Repeated rounds of plaque isolation and replating in the presence of Bluo-Gal resulted in the purification of the desired recombinant. Virus stocks were prepared by clarifying infected $RK_{13}$ cell lysates followed by centrifugation through a 36% sucrose cushion. Insertion of the MUC1 and B7.1 genes into the vaccinia genome was confirmed by Southern analysis using MUC1 and B7.1 gene probes. Expression of MUC1 and B7.1 protein was demonstrated by Western analysis using antibodies specific for each protein. More preferably, another cell line such as the monkey kidney cell line CV-1 (ATCC CCL 70) or chick embryo dermal (CED) cells would be used for vaccine production.

EXAMPLE 4

Construction and Characterization of Recombinant Avipox Virus Containing MUC1 and B7.1

The miMUC1 gene is inserted into a plasmid vector containing the vaccinia 40K promoter and the *E. coli* lacZ gene flanked by DNA sequences from the BamHI J region of the fowlpox genome. The resulting plasmid contains the miMUC1 gene under the control of the vaccinia virus 40K early/late promoter (Gritz et al., supra), and the lacZ gene under the control of the fowlpox Cl promoter (Jenkins et al., supra), all flanked by DNA sequences from the BamHI J region of the fowlpox genome. The parental virus used for the generation of this recombinant virus is the USDA licensed live fowlpox vaccine POXVAC-TC (Schering-Plough Corporation). The generation of recombinant vaccinia virus is accomplished via homologous recombination between fowlpox sequences in the POXVAC-TC fowlpox genome and the corresponding sequences in the plasmid vector in fowlpox-infected chick embryo dermal cells (CED), prepared as described (Jenkins et al., supra), transfected with the plasmid vector. Recombinant virus is identified using a chromogenic substrate for β-galactosidase (Bluo-Gal™). Viral plaques expressing lacZ appear blue against a clear background. Positive plaques are picked from the cell monolayer and their progeny are further propagated. Repeated rounds of plaque isolation and replating in the presence of Bluo-Gal result in the purification of the desired recombinant. Virus stocks are prepared by clarifying infected CED cell lysates followed by centrifugation through a 20% sucrose cushion. Insertion of the MUC1 gene into the fowlpox genome is confirmed by Southern analysis using a MUC1 gene probe. Expression of MUC1 protein is demonstrated by Western analysis using antibodies specific for MUC1.

Construction and characterization of a recombinant fowlpox virus containing both MUC1 and B7.1 is accomplished by inserting a promoter-B7.1 cassette into the plasmid described above, and by carrying out the manipulations described above.

Recombinant canary pox viruses containing MUC1 or MUC1 and B7.1 are constructed and characterized in an analogous fashion using canary pox as the parental virus (Taylor et al. (1991) Vaccine 9:190–193; Paoletti, U.S. Pat. No. 5,505,941).

EXAMPLE 5

1. Transfection and Transduction of the miMUC1 Gene in pLNSX

A 2 kb XhoI/XbaI restriction endonuclease fragment from pBs-miMUC1 was isolated and the ends repaired with DNA polymerase 1-Klenow fragment and ligated into the Stu I site of the retroviral vector pLNSX. The pLNSX-miMUC1 gene was transfected into the PA317 packaging cell line by Lipofectin (GIBCO/BRL) according to the manufacturer's instructions. Cells were harvested, plated onto 60 mm dishes, and incubated with 200–500 µg/ml G418 for three weeks. Clones of PA317 cells containing the miMUC1 gene were identified by Northern blot analysis of total RNA isolated from G418 resistant clones using the XbaI/XhoI DNA fragment of the miMUC1 gene as a radioactive probe. The retroviral supernatants of MUC1-transduced PA317 cells were collected and used to transduce MC38 cells in the presence of polybrene (8 µg/ml). Following transduction, MC38 cells were selected by cloning G418 resistant colonies and selection by FACs analysis using DF3 antibody. The resultant MUC1 positive cell line was designated MC38/MUC1. Those cells were shown to be negative for B7-1 expression by flow cytometry.

The amphotrophic packaging cell line PA317 was obtained from Dr. Robert Bassin (National Cancer Institute, NIH, Bethesda, Md.).

The MC38 murine colonic adenocarcinoma cell line (20) was obtained from the laboratory of Dr. Steve Rosenberg (National Cancer Institute, NIH, Bethesda, Md.).

EXAMPLE 6

FACS Analysis of Recombinant Protein Expression

Cell surface expression of MUC1 on MC38/MUC1 cells was analyzed by immunofluorescence. Cells were harvested and incubated at 4° C. for 30 minutes with 1 µg/ml DF3 MAb in 5% FBS-DPBS, followed by incubation with fluorescein-labeled goat anti-mouse IgG (Kirkegaard and Perry) for 30 minutes at 4° C. Analysis was performed with a FACScan (Becton-Dickinson Mountain View, Calif.).

Figure 2:
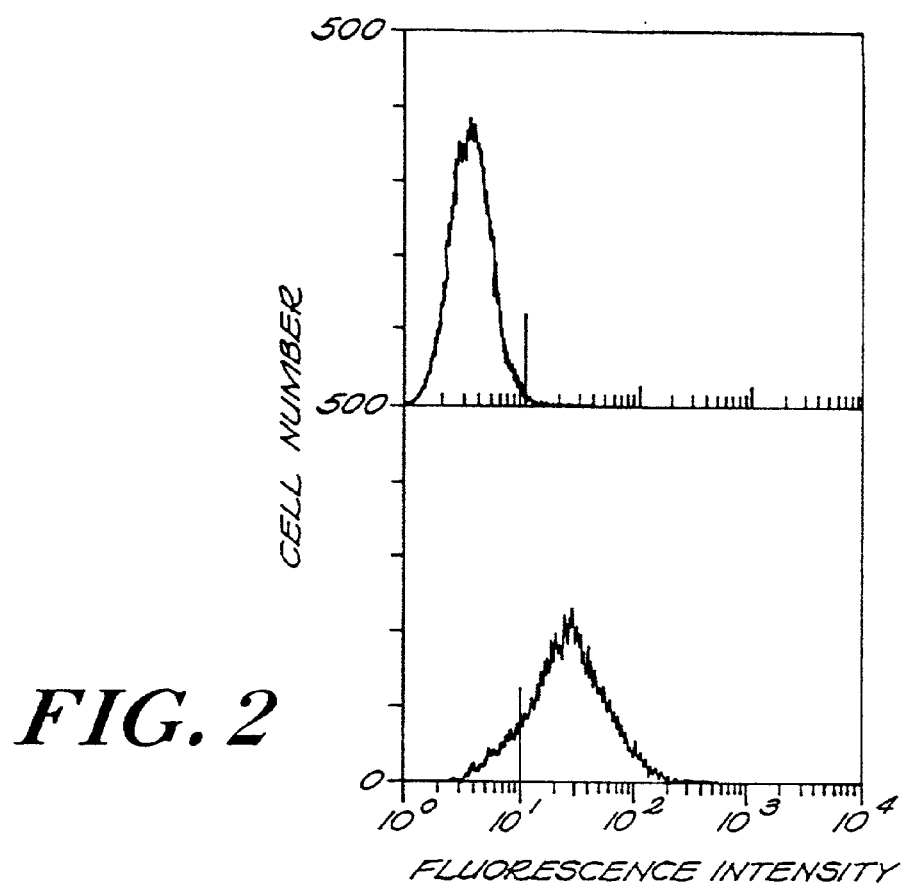
FIGS. 2A and 2B are graphs showing expression of MUC1 proteins in MC38 cells.

Surface expression of MUC1 glycoprotein in MUC1-transduced MC38 cells was examined by flow cytometry. FIGS. 2A and 2B illustrate that untransduced MC38 cells (FIG. 2A) do not react with DF3 MAb (98.5% of the cells are negative with a mean fluorescence of 20). However, MC38 cells transduced with the MUC1 gene (FIG. 2B) react strongly with the DF3 antibody (87.5% of the cells are positive with a mean fluorescence of 400). These studies thus demonstrate that MC38 tumor cells transduced with the miMUC1 gene (MC38/MUC1) express the MUC1 molecule.

EXAMPLE 7

Anti-Tumor Activity of Recombinant Vaccinia Virus Vaccine

A. Cytotoxicity Assay. To analyze the effect of rV-MUC1 or rV-MUC1/rV-B7 vaccination on MUC1 specific cytotoxic activity, splenic lymphocytes from mice inoculated with rV-MUC1 or the mixture of rV-MUC1 and rV-B7 were tested for their ability to lyse murine adenocarcinoma cells that were negative (MC38) or positive for MUC1 (MC38/MUC1) (Kantor, 3., et al. supra). Briefly, spleens were removed and mechanically dispersed through 70 mm cell strainers (Falcon, Becton Dickinson, Franklin Lakes, N3) to isolate single cell suspensions. Erythrocytes and dead cells were removed by centrifugation over a Ficoll-Hypaque gradient (density=1.119 g/ml) (Sigma Chemical Co., St. Louis, Mo.). MC38 cells and MC38/MUC1 cells were prepared for use as targets in a standard indium release assay as described previously (Hodge, J. W., et al. (1995) Cancer Res. 55:3598–603). Tumor cells ($2 \times 10^6$ cells) were radiolabeled with 50 µCi of $^{111}$In oxyquinoline solution (Amersham, Arlington Heights, Ill.) for 30 minutes at 37° C. and dispensed ($10^4$ cells/50 µl) into each well of 96-well U-bottom plates (Costar, Cambridge, Mass.). T-cells were added to effector to target (E:T) ratios of 100:1–12.5:1 in 96 well U-bottomed plates (Costar) and incubated for 16 hours at 37° C. with 5% $CO_2$. After incubation, supernatants were collected using a Supernatant Collection System (Skatron, Sterling, Va.) and radioactivity was quantitated using a gamma counter. (Cobra Autogamma, Packard, Downers Grove, Ill.). The percentage of specific release of $^{111}$In was determined by the standard equation: % specific lysis= [(experimental–spontaneous)/(maximum–spontaneous)]× 100.

Figure 3:
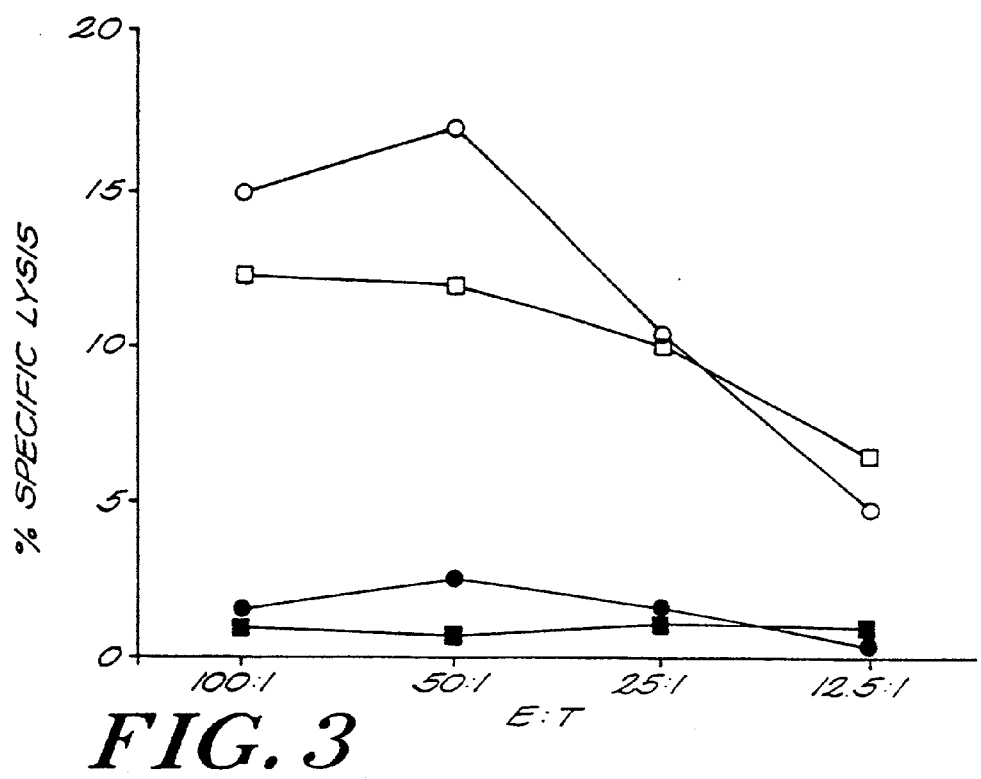
FIG. 3 is a graph illustrating primary CTL activity following immunization with an admixture of rV-MUC1 and rV-B7.

FIG. 3 shows the results of an experiment in which groups of mice were inoculated with an admixture of $10^7$ PFU rV-MUC1 and $10^7$ PFU V-Wyeth (squares), or an admixture of $10^7$ PFU rV-MUC1 and $10^7$ PFU rV-B7 (circles). All groups were inoculated with an admixture of $10^7$ PFU rV-MUC1 and $10^7$ PFU V-Wyeth after 14 and 28 days. Seven days following the final immunization, cytolytic activity was quantified against MC38 cells (MUC1 negative; closed symbols) or MC38/MUC1 cells (MUC1 positive; open symbols). T-cells from mice inoculated three times with rV-MUC1/V-Wyeth or one time with rV-MUC1/rV-B7 followed by two inoculations with rV-MUC1/V-Wyeth did not lyse the MUC1 negative MC38 targets (closed symbols), but did lyse the MUC1 positive MC38/MUC1 targets (open symbols). This MUC1 specific lysis was E:T ratio dependent.

B. Prevention of MUC1 Positive Pulmonary Metastases

Groups of C57BL/6 mice were inoculated subcutaneously with either (a) an admixture of $10^7$ PFU rV-B7 and $10^7$ PFU V-Wyeth; (b) an admixture of $10^7$ PFU rV-MUC1 and $10^7$ PFU V-Wyeth; or (c) an admixture of $10^7$ PFU rV-MUC1 and $10^7$ PFU rV-B7. After two weeks, mice in the first group were inoculated with $2 \times 10^7$ PFU V-Wyeth; while the remaining two groups were inoculated with an admixture of $10^7$ PFU rV-MUC1 and $10^7$ PFU V-Wyeth. Two weeks later, mice were challenged intravenously with $2 \times 10^6$ MC38/MUC1 tumor cells. Mice were euthanized 28 days following tumor transplant and experimental pulmonary metastatic nodules as defined by Wexler (Wexler, H., et al. (1966) J. Natl. Cancer Inst. 36:641–645) were stained. These metastatic nodules were enumerated in a blind fashion, and lungs with nodules too numerous to count were assigned an arbitrary value of >250.

Figure 4:
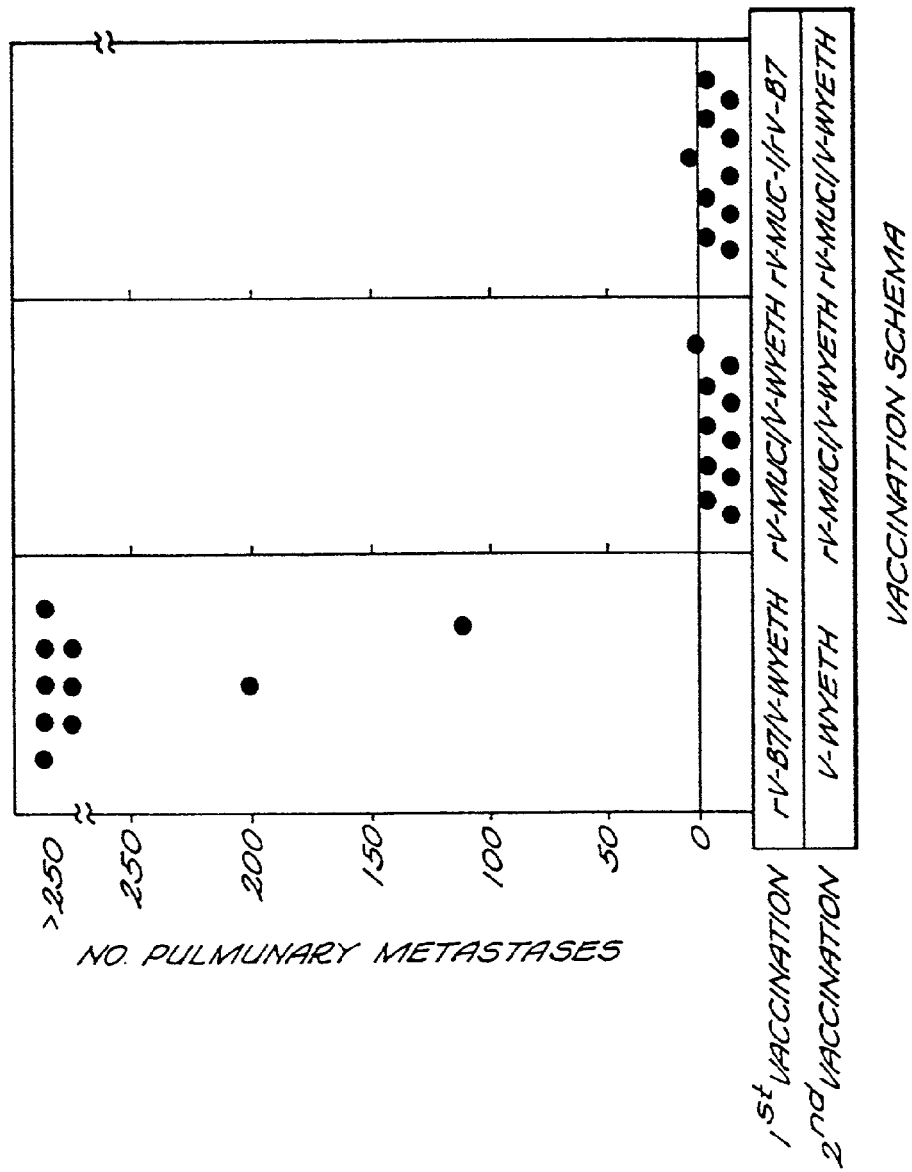
FIG. 4 is a graph showing prevention of MUC1-positive pulmonary metastases by immunization with rV-MUC1.

FIG. 4 illustrates the efficacy of rV-MUC1 in this experimental tumor model. Mice inoculated with rV-B7/V-Wyeth were all positive for lung metastases (8/10 mice had greater than 250 nodules). In contrast, 90% of mice inoculated with rV-MUC1/V-Wyeth and boosted with rV-MUC1/V-Wyeth remained free of pulmonary metastases (1/10 mice had 6 nodules). Similarly, 90% of mice receiving the same immunization scheme with the addition of rV-B7 in the first immunization remained free of pulmonary metastases.

C. Therapy of Established MUC1 Positive Pulmonary Metastases

C57BL/6 mice were challenged intravenously with $2\times10^6$ MC38/MUC1 tumor cells. After 3 days, mice were randomized and inoculated subcutaneously with either (a) $2\times10^7$ PFU V-Wyeth; (b) an admixture of $10^7$ PFU rV-B7 and $10^7$ PFU V-Wyeth; (c) an admixture of $10^7$ PFU rV-MUC1 and $10^7$ PFU V-Wyeth; or (d) an admixture of $10^7$ PFU rV-MUC1 and $10^7$ PFU rV-B7. Seven days later, mice in the first two groups were inoculated intravenously with $2\times10^7$ PFU V-Wyeth, while the remaining two groups were inoculated intravenously with an admixture of $10^7$ PFU rV-MUC1 and $10^7$ PFU V-Wyeth. Seven days later, following this inoculation, mice were inoculated a third time in a similar fashion. Mice were euthanized 28 days following tumor transplant and pulmonary metastatic nodules were stained and enumerated as above. Identically treated groups were followed for survival. Kaplan-Meier plots and Mantel-Cos (Logrank) tests were used to compare survival of mice belonging to different treatment groups.

Figure 5:
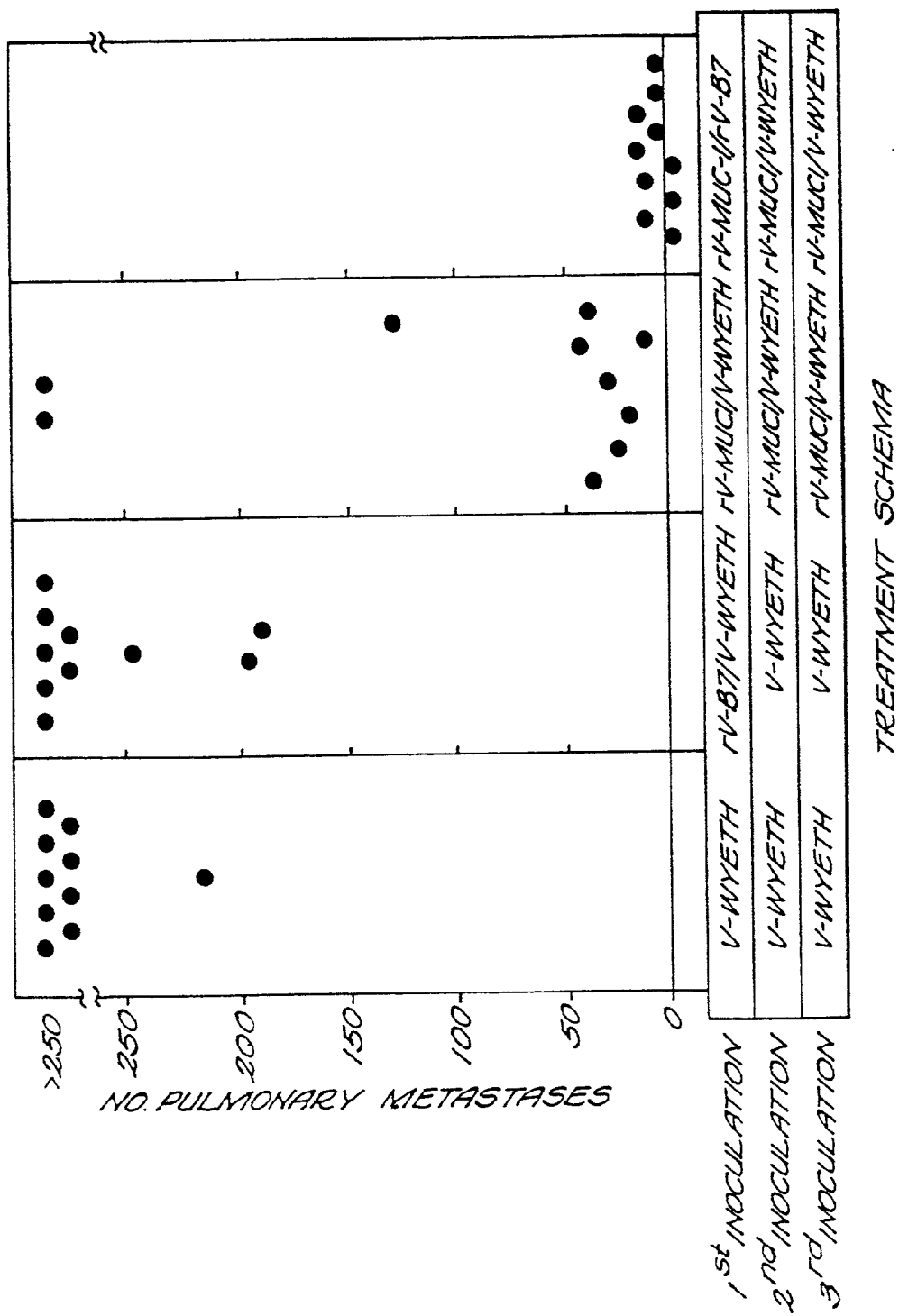
FIG. 5 is a graph illustrating treatment of established MUC1-positive pulmonary metastases by immunization with an admixture of rV-MUC1 and rV-B7.

FIG. 5 shows the efficacy of rV-MUC1 in a therapeutic setting. Mice inoculated with V-Wyeth or rV-B7/V-Wyeth were all positive for lung metastases (9/10 and 7/10, respectively had greater than 250 nodules.) Although all mice inoculated 3 times with rV-MUC1/V-Wyeth were positive for lung nodules, the number of metastases was comparatively low (7/10 with <50 nodules). In contrast, 30% of mice inoculated with rV-MUC1/rV-B7 and boosted with rV-MUC1/V-Wyeth remained free of pulmonary metastases, while the remaining mice all had less than 20 lung nodules.

Figure 6:
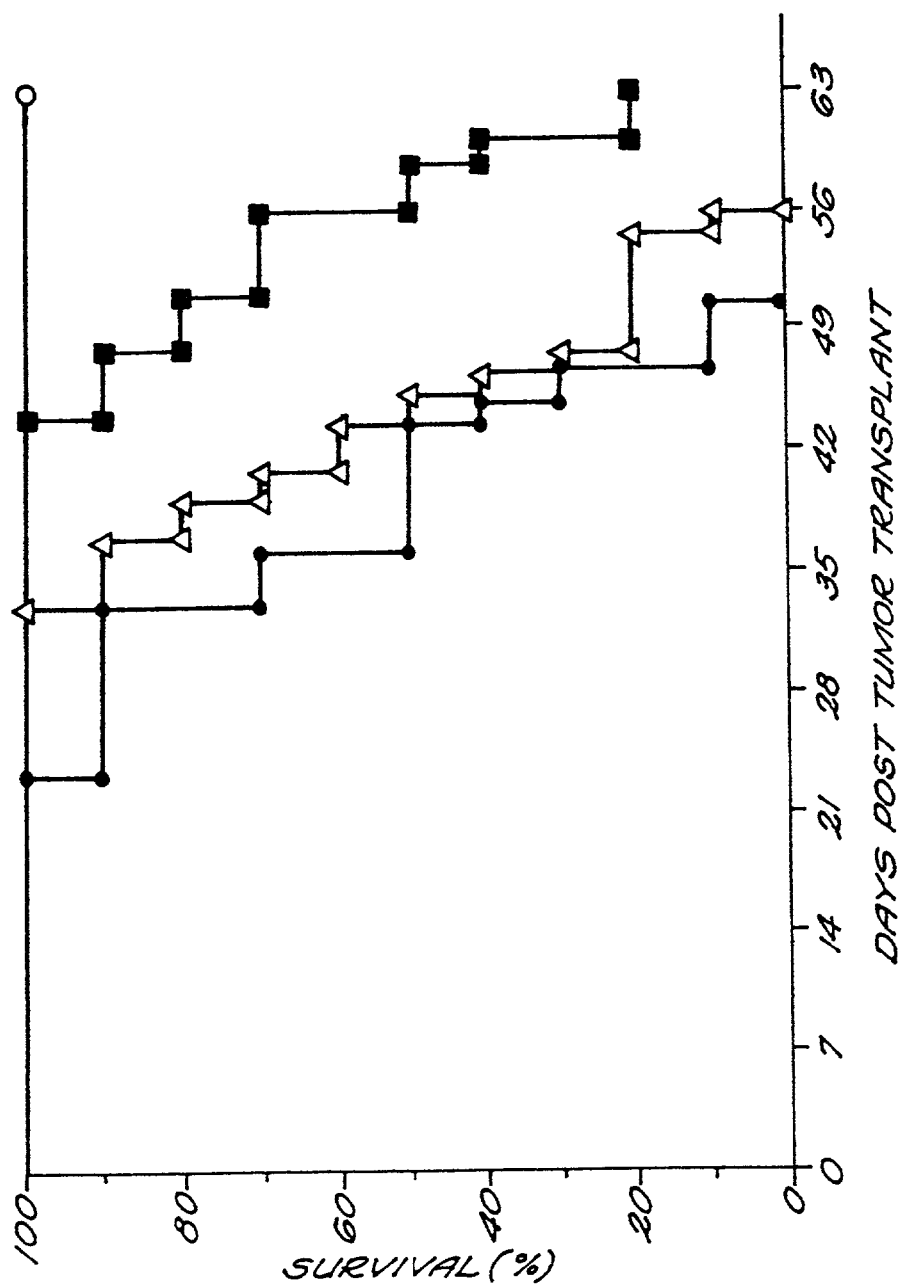
FIG. 6 is a graph illustrating survival of mice immunized with an admixture of rV-MUC1 and rV-B7.

FIG. 6 depicts a different parameter of therapy of established MUC1 positive pulmonary metastases in which a parallel group of mice was inoculated identically to those above and monitored for survival. In the experiment shown in FIG. 6, groups of 10 mice were transplanted intravenously with $2\times10^6$ MC38/MUC1 tumor cells, and tumors were allowed to establish for 3 days. Mice were inoculated every 7 days as in FIG. 5. Immunization sequences were: V-Wyeth: V-Wyeth: V-Wyeth (open triangles); rV-B7/V-Wyeth: V-Wyeth: V-Wyeth (closed circles); rV-MUC1/V-Wyeth: rV-MUC1/V-Wyeth: rV-MUC1/V-Wyeth: rV-MUC1/V-Wyeth (closed squares); and rV-MUC1/rV-B7: rV-MUC 1/V-Wyeth: rV-MUC1/V-Wyeth (open circles). Vaccination of mice with V-Wyeth or rV-B7/V-Wyeth and boosting with V-Wyeth had no effect on mouse survival, with 100% mortality by 50–56 days post tumor challenge. In contrast, inoculation of mice three times with rV-MUC1/V-Wyeth resulted in a significant improvement of survival time (p=0.0009–<0.0001). Furthermore, immunization of mice with rV-MUC1/rV-B7 followed by two boosts with rV-MUC1/V-Wyeth resulted in 100% survival of mice (p<0.0001). It thus appears that the administration of rV-MUC1 can significantly improve the survival of mice bearing MUC1 positive tumors, but only the admixture of rV-MUC1 with rV-B7 can completely eradicate MUC1 expressing tumors. Lungs of these animals were examined at day 65 and were free of tumor nodules.

The recombinant pox viruses of the present invention provide significant advantages. For example, previously described recombinant vaccinia viruses encoding MUC1 can undergo significant genetic deletion thereby destabilizing the virus, decreasing antigen immunogenicity, and reducing vaccine efficacy. In contrast, the present recombinant pox viruses encode an immunogenic MUC1 fragment that does not undergo significant genetic deletion, thereby providing an unexpectedly stable and immunogenic pox virus. Accordingly, efficacy of vaccines including the present recombinant pox viruses is substantially increased. Propagation of the present recombinant pox viruses is positively impacted by the stability of the immunogenic MUC1 fragment, e.g., by providing uniform isolation of desired viral strains. Importantly, vaccine efficacy against established or pre-existing MUC1 expressing tumors is potentiated by providing an immunomodulator such as a T-cell co-stimulatory factor, particularly as an admixture with another recombinant pox virus encoding the T-cell co-stimulatory factor.

All publications, patents, and patent applications mentioned in the specification are indicative of the level of skill of those in the art to which this invention pertains. All publications, patents, and patent applications are fully incorporated herein by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant pox virus comprising a nucleic acid sequence encoding an immunogenic MUC1 fragment comprising 5 to 25 MUC1 tandem repeat units, the nucleic acid sequence comprising
    a first nucleotide sequence encoding the amino acid sequence of SEQ ID NO:1 that is SEQ ID NO:2; and
    a second nucleotide sequence encoding 2 to 24 copies of the amino acid sequence of SEQ ID NO:1 wherein, the second nucleotide sequence comprising 2 to 24 copies of an altered nucleotide-sequence of SEQ ID NO:2 that is altered by changing wobbled nucleotides of the codons of SEQ ID NO:2.

2. The recombinant pox virus of claim 1, wherein the immunogenic MUC1 fragment comprises 6 to 14 tandem repeat units.

3. The recombinant pox virus of claim 2, wherein the immunogenic MUC1 fragment comprises 9 tandem repeat units.

4. The recombinant pox virus of claim 1, wherein the pox virus is selected from the group consisting of *orthopox*, suipox and avipox.

5. A pharmaceutical composition comprising a recombinant pox virus comprising a nucleic acid sequence encoding an immunogenic MUC1 fragment comprising 5 to 25 MUC1 tandem repeat units, the nucleic acid sequence comprising
    a first nucleotide sequence encoding the amino acid sequence of SEQ ID NO:1 that is SEQ ID NO:2;
    a second nucleotide sequence encoding 2 to 24 copies of the amino acid sequence of SEQ ID NO:1 wherein, the second nucleotide sequence comprising 2 to 24 copies of an altered nucleotide sequence of SEQ ID NO:2 is altered by changing wobbled nucleotides of the codons of SEQ ID NO:2; and
    a third nucleotide sequence encoding an immunomodulator.

6. The pharmaceutical composition of claim 5, wherein the immunomodulator is selected from the group consisting of T-cell co-stimulatory factors and cytokines.

7. The pharmaceutical composition of claim 6, wherein the cytokine is an interleukin.

8. The pharmaceutical composition of claim 5, wherein the immunomodulator is both a T-cell co-stimulatory factor and a cytokine.

9. The recombinant pox virus of claim 5, wherein the pox virus is selected from the group consisting of *orthopox*, suipox and avipox.

10. The pharmaceutical composition of claim 5, wherein said MUC1 fragment comprises about 6 to 14 tandem repeat units.

11. A method of generating an immune response in a mammal having a MUC1-expressing tumor, the method comprising:
    (a) administering to the mammal the pox virus of claim 1 as a first pox virus; and
    (b) administering an amount of a second pox virus selected from the group consisting of *orthopox*, suipox and avipox.

12. The method of claim 11, wherein the second pox virus is from a viral genus different from said pox virus of step (a).

13. The method of claim 11, further comprising administering to the mammal an immunomodulator.

14. A method for generating an immune response in a mammal that contains a MUC1-expressing tumor, the method comprising administering to said mammal the pox virus of claim 4.

15. The recombinant pox virus of claim 1, wherein the pox virus is MVA.

16. The method of claim 13, wherein the immunomodulator is a cytokine or a co-stimulatory molecule.

17. The method of claim 16, wherein said co-stimulatory molecule is B7.

18. The method of claim 17, wherein said B7 is B7.1 or B7.2.

19. The method of claim 16, wherein the cytokine is an interleukin.

20. The method of claim 11, wherein said first pox virus is selected from the group consisting of an orthopox virus vector, an avipox virus vector, a suipox virus vector, and a capripox virus vector.

21. The method of claim 20, wherein the first pox virus is an orthopox virus.

22. The method of claim 21, wherein the orthopox virus is a vaccinia virus.

23. The method of claim 21, wherein the vaccinia virus is an MVA.

24. The method of claim 11, wherein the first pox virus is an orthopox virus and the second pox virus is an avipox virus.

25. The method of claim 24, wherein the avipox virus is a fowipox virus.

26. The method of claim 24, wherein the orthopox virus is a vaccinia virus.

27. The method of claim 26, wherein the vaccinia virus is MVA.

28. The method of claim 11, wherein said first pox virus further comprises a nucleic acid sequence encoding an immunomodulator.

29. The method of claim 11 or 28, wherein the second pox virus further comprises a nucleic acid sequence encoding an immunomodulator.

30. The recombinant pox virus of claim 1, wherein at least one of the copies of an altered nucleotide sequence is selected from the group consisting of SEQ ID NOS: 4–12.

31. The pharmaceutical composition of claim 5, wherein at least one of the copies of an altered nucleotide sequence is selected from the group consisting of SEQ ID NOS: 4–12.

32. The method of claim 11, wherein at least one of the copies of an altered nucleotide sequence is selected from the group consisting of SEQ ID NOS: 4–12.

33. A recombinant pox virus comprising a nucleic acid sequence encoding an immunogenic MUC1 fragment comprising 5 to 25 MUC1 tandem repeat units, the nucleic acid sequence comprising a first nucleotide sequence having SEQ ID NO:2; and a second nucleotide sequence comprising 2 to 24 altered nucleotide sequences encoding 2 to 24 altered tandem repeats, wherein each altered tandem repeat is altered from SEQ ID NO:2 by changing at least one nucleotide of at least one codon of SEQ ID NO: 2 so that the amino acid of SEQ ID NO: 1 is maintained or by substituting at least one codon in SEQ ID NO:1 such that such substituted codons is selected from the group consisting of substituting at least one of the glycines in the SEQ ID NO:1 to serine, substituting at least one of the serines in the SEQ ID NO:1 to glycine, and substituting the valine in the SEQ ID NO:1 to leucine.

34. A recombinant pox virus comprising a nucleic acid sequence encoding an immunogenic MUC1 fragment comprising 6 identical amino acid tandem repeat units, the nucleic acid sequence comprising a first nucleotide sequence encoding the amino acid sequence of SEQ ID NO:1 that is SEQ ID NO:2; and a second nucleotide sequence encoding 5 copies of the amino acid sequence of SEQ ID NO:1 as the other 5 tandem repeat units, the second amino acid sequence comprising 5 copies of an altered nucleotide sequence of SEQ ID NO:2 by changing wobbled nucleotides of the codons of SEQ ID NO:2, the 5 copies encoding the other 5 tandem repeat units.

35. A recombinant pox virus comprising nucleic acid sequences encoding 5 to 25 MUC1 tandem repeat units, said tandem repeat units having an amino acid sequence of SEQ ID NO:1, wherein at least one of the nucleic acid sequences encoding the tandem repeats has SEQ ID NO:2 and at least one of other nucleic acid sequences encoding the tandem repeats is altered to reduce duplications of codons.

36. The recombinant pox virus of claim 35, wherein at least one nucleic acid encoding the tandem repeats is altered by changing wobbled nucleotides of codons of SEQ ID NO:2.

37. The recombinant pox virus of claim 35, wherein at least one nucleic acid encoding the tandem repeats is altered by the third base of threonine codons 3, 11 and 16 of SEQ ID NO: 2 using ACG, ACT, and ACA respectively.

* * * * *

SEQUENCE LISTING

<160> NUMBER OF SEQ ID NOS: 20

<210> SEQ ID NO 1
<211> LENGTH: 20
<212> TYPE: PRT
<213> ORGANISM: Homo sapiens

<400> SEQUENCE: 1

Gly Ser Thr Ala Pro Pro Ala His Gly Val Thr Ser Ala Pro Asp Thr
 1               5                  10                  15

Arg Pro Ala Pro
            20

<210> SEQ ID NO 2
<211> LENGTH: 60

```
<212> TYPE: DNA
<213> ORGANISM: Homo sapiens

<400> SEQUENCE: 2
ggctccaccg cccccccagc ccacggtgtc acctcggccc cggacaccag gccggcccg        60

<210> SEQ ID NO 3
<211> LENGTH: 7
<212> TYPE: PRT
<213> ORGANISM: Homo sapiens

<400> SEQUENCE: 3

Pro Asp Thr Arg Pro Ala Pro
  1               5

<210> SEQ ID NO 4
<211> LENGTH: 60
<212> TYPE: DNA
<213> ORGANISM: Homo sapiens

<400> SEQUENCE: 4
ggcagtactg caccaccggc acatggcgta acatcagcac ctgatacaag acctgcacct        60

<210> SEQ ID NO 5
<211> LENGTH: 60
<212> TYPE: DNA
<213> ORGANISM: Homo sapiens

<400> SEQUENCE: 5
ggatccaccg cgccgcctgc gcacggagtg acgtcggcgc ccgacacgcg ccccgctccc        60

<210> SEQ ID NO 6
<211> LENGTH: 60
<212> TYPE: DNA
<213> ORGANISM: Homo sapiens

<400> SEQUENCE: 6
gggtcaacag ctcctcccgc tcatggggtt acttctgctc cagatactcg cccagctcca        60

<210> SEQ ID NO 7
<211> LENGTH: 60
<212> TYPE: DNA
<213> ORGANISM: Homo sapiens

<400> SEQUENCE: 7
ggttcgacgg ccccccctgc tcacggtgta acatccgccc cggataccag accggcccct        60

<210> SEQ ID NO 8
<211> LENGTH: 60
<212> TYPE: DNA
<213> ORGANISM: Homo sapiens

<400> SEQUENCE: 8
ggcagcaccg caccgcccgc acacggggtc acaagcgcgc cagacactcg acctgcgcca        60

<210> SEQ ID NO 9
<211> LENGTH: 60
<212> TYPE: DNA
<213> ORGANISM: Homo sapiens

<400> SEQUENCE: 9
ggaagtaccg ctccacctgc acacggggtc acaagcgcgc cagacactcg acctgcgcca        60
```

```
<210> SEQ ID NO 10
<211> LENGTH: 60
<212> TYPE: DNA
<213> ORGANISM: Homo sapiens

<400> SEQUENCE: 10
gggtcgactg ccctccggc gcatggtgtg acctcagctc ctgacacaag gccagcccca      60

<210> SEQ ID NO 11
<211> LENGTH: 60
<212> TYPE: DNA
<213> ORGANISM: Homo sapiens

<400> SEQUENCE: 11
ggttcaacgg cacctccagc acacggagtc acgtctgcac ccgacacccg tccagctccg      60

<210> SEQ ID NO 12
<211> LENGTH: 60
<212> TYPE: DNA
<213> ORGANISM: Homo sapiens

<400> SEQUENCE: 12
ggtagtacag cgccacccgc acatggcgtc acgagcgctc cggatacgag accggcgcct      60

<210> SEQ ID NO 13
<211> LENGTH: 78
<212> TYPE: DNA
<213> ORGANISM: Homo sapiens

<400> SEQUENCE: 13
ggctccaccg cacccccagc ccacggtgtc acctcggccc cggacaccag gcgggccccg      60
ggctccaccc cggccccg                                                   78

<210> SEQ ID NO 14
<211> LENGTH: 60
<212> TYPE: DNA
<213> ORGANISM: Homo sapiens

<400> SEQUENCE: 14
ggctccaccg cccccccagc ccatggtgtc acctcggccc cggacaacag gcccgccttg      60

<210> SEQ ID NO 15
<211> LENGTH: 39
<212> TYPE: DNA
<213> ORGANISM: Homo sapiens

<400> SEQUENCE: 15
ggctccaccg ccctccagt ccacaatgtc acctcggcc                             39

<210> SEQ ID NO 16
<211> LENGTH: 20
<212> TYPE: PRT
<213> ORGANISM: Homo sapiens

<400> SEQUENCE: 16

Gly Ser Thr Ala Pro Pro Ala His Gly Val Thr Ser Ala Pro Asp Thr
 1               5                  10                  15

Arg Arg Ala Pro
            20

<210> SEQ ID NO 17
<211> LENGTH: 20
<212> TYPE: PRT
```

<213> ORGANISM: Homo sapiens

<400> SEQUENCE: 17

Gly Ser Thr Ala Pro Pro Ala His Gly Val Thr Ser Ala Pro Asp Asn
 1               5                  10                  15

Arg Pro Ala Leu
            20

<210> SEQ ID NO 18
<211> LENGTH: 13
<212> TYPE: PRT
<213> ORGANISM: Homo sapiens

<400> SEQUENCE: 18

Gly Ser Thr Ala Pro Pro Val His Asn Val Thr Ser Ala
 1               5                  10

<210> SEQ ID NO 19
<211> LENGTH: 1527
<212> TYPE: DNA
<213> ORGANISM: Homo sapiens

<400> SEQUENCE: 19

| | | | | | |
|---|---|---|---|---|---|
| atgacaccgg | gcacccagtc | tcctttcttc | ctgctgctgc | tcctcacagt | gcttacagct | 60 |
| accacagccc | ctaaacccgc | aacagttgtt | acgggttctg | gtcatgcaag | ctctacccca | 120 |
| ggtggagaaa | aggagacttc | ggctacccag | agaagttcag | tgcccagctc | tactgagaag | 180 |
| aatgctgtga | gtatgacaag | cttgatatcg | aattccggtg | tccggggctc | accgccccc | 240 |
| ccagcccacg | gtgtcacctc | ggccccggac | accaggccgg | ccccgggctc | accgccccc | 300 |
| ccagcccacg | gtgtcacctc | ggccccggac | accaggccgg | ccccgggctc | accgccccc | 360 |
| ccagcccacg | gtgtcacctc | ggccccggac | accaggccgg | ccccgggctc | accgcaccc | 420 |
| ccagcccacg | gtgtcacctc | ggccccggac | accaggcggg | ccccgggctc | acccccggcc | 480 |
| ccgggctcca | ccgcccccc | agcccacggt | gtcacctcgg | ccccggacac | caggccggcc | 540 |
| ccgggctcca | ccgcccccc | agcccatggt | gtcacctcgg | ccccggacaa | caggcccgcc | 600 |
| ttgggctcca | ccgcccctcc | agtccacaat | gtcacctcgg | cctcaggctc | tgcatcaggc | 660 |
| tcagcttcta | ctctggtgca | caacggcacc | tctgccaggg | ctaccacaac | ccagccagc | 720 |
| aagagcactc | cattctcaat | tcccagccac | cactctgata | ctcctaccac | ccttgccagc | 780 |
| catagcacca | agactgatgc | cagtagcact | caccatagca | cggtacctcc | tctcacctcc | 840 |
| tccaatcaca | gcacttctcc | ccagttgtct | actggggtct | ctttcttttt | cctgtctttt | 900 |
| cacatttcaa | acctccagtt | tccttcctct | ctcgaagatc | ccagcaccga | ctactaccaa | 960 |
| gagctgcaga | gagacatttc | tcaaatgttt | ttgcagattt | ataaacaagg | ggttttctg | 1020 |
| ggcctctcca | atattaagtt | caggccagga | tctgtgctgg | tacaattgac | tctgccttc | 1080 |
| cgagaaggta | ccatcaatgt | ccacgacgtg | agacacagt | tcaatcagta | taaaacggaa | 1140 |
| gcagcctctc | gatataacct | gacgatccca | gacgtcagcg | tgagtgatgt | gccatttcct | 1200 |
| ttctctgccc | agtctggggc | tggggtgcca | ggctggggca | tcgcgctgct | cctgctggtc | 1260 |
| tgtgttctgg | ttgcgctggc | cattgtctat | ctcattgcct | tggctgtctg | tcagtgccgc | 1320 |
| cgaaagaact | acgggcagct | ggacatcttt | ccagcccggg | ataccaccaa | tcctatgagc | 1380 |
| gagtaccccc | cctaccacac | ccatgggcgc | tatgtcccc | ctagcagtac | cgatcgtagc | 1440 |
| ccctatgaga | aggtttctgc | aggtaatggt | ggcagcagcc | tctcttacac | aaacccagca | 1500 | gtggcagcca cttctgccaa cttgtag                                          1527

<210> SEQ ID NO 20
<211> LENGTH: 508
<212> TYPE: PRT
<213> ORGANISM: Homo sapiens

<400> SEQUENCE: 20

Met Thr Pro Gly Thr Gln Ser Pro Phe Phe Leu Leu Leu Leu Leu Thr
1               5                   10                  15

Val Leu Thr Ala Thr Ala Pro Lys Pro Ala Thr Val Val Thr Gly
            20                  25                  30

Ser Gly His Ala Ser Ser Thr Pro Gly Gly Glu Lys Glu Thr Ser Ala
            35                  40                  45

Thr Gln Arg Ser Ser Val Pro Ser Ser Thr Glu Lys Asn Ala Val Ser
        50                  55                  60

Met Thr Ser Leu Ile Ser Asn Ser Gly Val Arg Gly Ser Thr Ala Pro
65                  70                  75                  80

Pro Ala His Gly Val Thr Ser Ala Pro Asp Thr Arg Pro Ala Pro Gly
                85                  90                  95

Ser Thr Ala Pro Pro Ala His Gly Val Thr Ser Ala Pro Asp Thr Arg
            100                 105                 110

Pro Ala Pro Gly Ser Thr Ala Pro Pro Ala His Gly Val Thr Ser Ala
        115                 120                 125

Pro Asp Thr Arg Pro Ala Pro Gly Ser Thr Ala Pro Pro Ala His Gly
    130                 135                 140

Val Thr Ser Ala Pro Asp Thr Arg Arg Ala Pro Gly Ser Thr Pro Ala
145                 150                 155                 160

Pro Gly Ser Thr Ala Pro Pro Ala His Gly Val Thr Ser Ala Pro Asp
                165                 170                 175

Thr Arg Pro Ala Pro Gly Ser Thr Ala Pro Pro Ala His Gly Val Thr
            180                 185                 190

Ser Ala Pro Asp Asn Arg Pro Ala Leu Gly Ser Thr Ala Pro Pro Val
        195                 200                 205

His Asn Val Thr Ser Ala Ser Gly Ser Ala Ser Gly Ser Ala Ser Thr
    210                 215                 220

Leu Val His Asn Gly Thr Ser Ala Arg Ala Thr Thr Thr Pro Ala Ser
225                 230                 235                 240

Lys Ser Thr Pro Phe Ser Ile Pro Ser His His Ser Asp Thr Pro Thr
                245                 250                 255

Thr Leu Ala Ser His Ser Thr Lys Thr Asp Ala Ser Ser Thr His His
            260                 265                 270

Ser Thr Val Pro Pro Leu Thr Ser Ser Asn His Ser Thr Ser Pro Gln
        275                 280                 285

Leu Ser Thr Gly Val Ser Phe Phe Leu Ser Phe His Ile Ser Asn
    290                 295                 300

Leu Gln Phe Pro Ser Ser Leu Glu Asp Pro Ser Thr Asp Tyr Tyr Gln
305                 310                 315                 320

Glu Leu Gln Arg Asp Ile Ser Gln Met Phe Leu Gln Ile Tyr Lys Gln
                325                 330                 335

Gly Gly Phe Leu Gly Leu Ser Asn Ile Lys Phe Arg Pro Gly Ser Val
            340                 345                 350

Leu Val Gln Leu Thr Leu Ala Phe Arg Glu Gly Thr Ile Asn Val His
        355                 360                 365

```
-continued

Asp Val Glu Thr Gln Phe Asn Gln Tyr Lys Thr Glu Ala Ala Ser Arg
    370             375             380

Tyr Asn Leu Thr Ile Pro Asp Val Ser Val Ser Asp Val Pro Phe Pro
385             390             395             400

Phe Ser Ala Gln Ser Gly Ala Gly Val Pro Gly Trp Gly Ile Ala Leu
            405             410             415

Leu Leu Leu Val Cys Val Leu Val Ala Leu Ala Ile Val Tyr Leu Ile
            420             425             430

Ala Leu Ala Val Cys Gln Cys Arg Arg Lys Asn Tyr Gly Gln Leu Asp
            435             440             445

Ile Phe Pro Ala Arg Asp Thr Tyr His Pro Met Ser Glu Tyr Pro Thr
    450             455             460

Tyr His Thr His Gly Arg Tyr Val Pro Pro Ser Ser Thr Asp Arg Ser
465             470             475             480

Pro Tyr Glu Lys Val Ser Ala Gly Asn Gly Gly Ser Ser Leu Ser Tyr
            485             490             495

Thr Asn Pro Ala Val Ala Ala Thr Ser Ala Asn Leu
            500             505
```